United States Patent
Abdo et al.

(10) Patent No.: US 11,435,294 B2
(45) Date of Patent: Sep. 6, 2022

(54) COLOR-CHANGING ENVIRONMENTAL STIMULUS INDICATOR WITH REFERENCE OF VARIABLE APPEARANCE

(71) Applicant: Temptime Corporation, Morris Plains, NJ (US)

(72) Inventors: Mohannad Abdo, Clifton, NJ (US); Frederick Robert Grabiner, Livingston, NJ (US); Dawn E. Smith, Martinsville, NJ (US)

(73) Assignee: TEMPTIME CORPORATION, Morris Plains, NJ (US)

( * ) Notice: Subject to any disclaimer, the term of this patent is extended or adjusted under 35 U.S.C. 154(b) by 435 days.

(21) Appl. No.: 15/723,693

(22) Filed: Oct. 3, 2017

(65) Prior Publication Data

US 2018/0100807 A1    Apr. 12, 2018

Related U.S. Application Data

(60) Provisional application No. 62/407,222, filed on Oct. 12, 2016.

(51) Int. Cl.
*G01N 21/78* (2006.01)
*C09D 11/50* (2014.01)
(Continued)

(52) U.S. Cl.
CPC ............. *G01N 21/78* (2013.01); *A61K 39/00* (2013.01); *C09D 11/50* (2013.01); *G01N 31/22* (2013.01);
(Continued)

(58) Field of Classification Search
CPC ........ G01N 21/78; G01N 31/22; A61K 39/00; C09D 11/50
(Continued)

(56) References Cited

U.S. PATENT DOCUMENTS 3,999,946 A * 12/1976 Patel .................... G01N 31/229
422/400
4,228,126 A    10/1980 Patel et al.
(Continued)

FOREIGN PATENT DOCUMENTS

WO    WO-2013170273 A2 * 11/2013 ............. G01N 21/78

OTHER PUBLICATIONS

World Health Organization: Vaccine Vial Monitors: FAQs. 2011. https://www.who.int/immunization/programmes_systems/supply_chain/optimize/vaccine_vial_monitors_faqs.pdf?ua=1 (Year: 2011).*
(Continued)

*Primary Examiner* — Benjamin R Whatley
*Assistant Examiner* — Jacqueline Brazin
(74) *Attorney, Agent, or Firm* — K&L Gates LLP

(57) ABSTRACT

A color-changing environmental stimulus indicator includes a substrate, an active indicator placed above the substrate, and a reference component. The active indicator is configured to change color in response to an environmental stimulus. The reference component is also color changeable in response to an environmental stimulus. The reference component is configured to have a similar appearance to the active indicator at an end point. The environmental stimulus includes one or more of temperature, cumulative temperature, humidity, pH, and ultraviolet radiation.

26 Claims, 8 Drawing Sheets

(51) Int. Cl.
   *A61K 39/00* (2006.01)
   *G01N 31/22* (2006.01)
   *G01N 21/77* (2006.01)
   *G01N 21/81* (2006.01)
   *G01N 21/80* (2006.01)

(52) U.S. Cl.
   CPC ............. *G01N 21/80* (2013.01); *G01N 21/81* (2013.01); *G01N 2021/7786* (2013.01)

(58) Field of Classification Search
   USPC ........................................................ 422/409
   See application file for complete search history.

(56) References Cited

U.S. PATENT DOCUMENTS

| | | | |
|---|---|---|---|
| 4,298,348 A | 11/1981 | Ivory | |
| 4,788,151 A | 11/1988 | Preziosi et al. | |
| 6,524,000 B1 | 2/2003 | Roth | |
| 2003/0053377 A1* | 3/2003 | Spevacek | G01K 3/04 |
| | | | 368/327 |
| 2009/0131718 A1 | 5/2009 | Baughman et al. | |
| 2016/0011157 A1* | 1/2016 | Smyth | G01N 21/78 |
| | | | 422/426 |
| 2016/0349224 A1* | 12/2016 | Patel | G01N 31/229 |

OTHER PUBLICATIONS

Wegner et al. "Topochemical Reactions of Monomers with Conjugated Triple Bonds" 9 J. Poly. Sci.B.Poly.Letters 133-44 (1971).
Wegner "Topochemical Polymerization of Monomers with Conjugated Triple Bonds", 154 Die Makromoleculare Chemie 35-48 (1972).

* cited by examiner

| 37°C | OD | | | |
|---|---|---|---|---|
| Days | 1) Active Indicator | 2) Active Reference | Active Reference - Indicator | Constant Reference - Indicator |
| 0.00 | 0.093 | 0.492 | 0.40 | 0.40 |
| 1.67 | 0.287 | 0.538 | 0.25 | 0.21 |
| 2.51 | 0.368 | 0.562 | 0.19 | 0.12 |
| 3.52 | 0.458 | 0.601 | 0.14 | 0.03 |
| 5.15 | 0.570 | 0.635 | 0.06 | -0.08 |
| 7.22 | 0.699 | 0.700 | 0.00 | -0.21 |
| 8.88 | 0.828 | 0.760 | -0.07 | -0.34 |

| 45°C | OD | | | |
|---|---|---|---|---|
| Days | 1) Active Indicator | 2) Active Reference | Active Reference - Indicator | Constant Reference - Indicator |
| 0.00 | 0.093 | 0.492 | 0.40 | 0.40 |
| 0.69 | 0.320 | 0.547 | 0.23 | 0.17 |
| 1.42 | 0.466 | 0.601 | 0.13 | 0.03 |
| 1.61 | 0.502 | 0.607 | 0.11 | -0.01 |
| 2.29 | 0.631 | 0.660 | 0.03 | -0.14 |

FIG. 7

COLOR-CHANGING ENVIRONMENTAL STIMULUS INDICATOR WITH REFERENCE OF VARIABLE APPEARANCE

CROSS-REFERENCE TO RELATED APPLICATIONS

This application claims priority to U.S. Provisional Application No. 62/407,222, filed Oct. 12, 2016, the entire disclosure of which is incorporated herein by reference.

BACKGROUND

Many commercial products are sensitive to environmental stimuli, such as temperature, cumulative temperature, humidity, pH, and ultraviolet radiation, and may lose efficacy or quality under any of these conditions. Examples of such commercial products include certain pharmaceuticals, medical products, and foodstuffs as well as some industrial products. Conventional environmental indicators to detect such changes typically use a constant/fixed-color reference to show an end point appearance of the active indicator/area. The end point appearance may be an appearance such as a dark appearance that indicates a probable condition of an associated host product, for example, that the host product has lost efficacy or quality and should not be used.

SUMMARY

The present disclosure provides new and innovative color-changing environmental stimulus indicators having a color changing reference. In some embodiments, a color-changing environmental stimulus indicator includes a substrate, an active indicator placed above the substrate, and a reference component. The active indicator and the reference component are color changeable in response to an environmental stimulus. In some embodiments, the active indicator and the reference component change color in response to the same environmental stimulus. In other embodiments, the active indicator and the reference component change color in response to different environmental stimuli. The environmental stimulus includes one or more of temperature, cumulative temperature, humidity, pH, and ultraviolet radiation.

In some embodiments, the active indicator is configured to darken in response to exposure to the environmental stimulus and the reference component is configured to lighten in response to exposure to the environmental stimulus. In other embodiments, both the active indicator and the reference component are configured to darken (or lighten) in response to exposure to the environmental stimulus. In some embodiments, the active indicator or the reference component is a color changing ink, such as a diacetylene. In other embodiments, the active indicator or the reference component change color by using a technique selected from the group consisting of metal etching, dye diffusion, acid/base reactions, and combinations thereof. The color change is at least one of a change in color, color density, fluorescence, or opacity.

In some embodiments, the reference component is configured to change color with time. In some embodiments, the color change of the active indicator and the reference is irreversible and occurs after a predetermined cumulative exposure to the environmental stimulus. The reference component is configured to have a similar appearance to the active indicator at an end point. In some embodiments, the color-changing environmental stimulus indicator includes an ultraviolet radiation filter configured to protect the active indicator or the reference component from exposure to ultraviolet radiation. In some embodiments, an active ink is added to the reference component. The active ink is configured to change color quickly at the beginning of the exposure and stabilize at later times.

In some embodiments, both the active indicator and the reference component are configured to darken in response to exposure to cumulative temperature at different rates such that the color-changing environmental stimulus indicator has a higher effective activation energy than the active indicator. In other embodiments, the active indicator and the reference component are configured to darken in response to exposure to ultraviolet radiation and temperature. Then, a temperature-insensitive monomer is coated over the reference component to match the darkening of the active indicator in the presence of ultraviolet light.

In some embodiments, the active indicator is configured to change color in response to exposure to temperature, and the reference component is configured to change color in response to exposure to at least one of humidity, pH, and ultraviolet radiation. In some embodiments, the active indicator is configured to darken in response to exposure to the temperature and the reference component is configured to lighten in response to exposure to the at least one of humidity, pH, and ultraviolet radiation.

In some embodiments, the active indicator is configured to change color in response to exposure to temperature and low humidity, and the reference component is configured to change color in response to exposure to the low humidity to offset the effect of the low humidity to the active indicator. In some embodiments, the active indicator is configured to change color in response to exposure to cumulative temperature and the reference component is configured to change color in response to exposure to a temperature near or below a predetermined temperature.

In some embodiments, a color-changing environmental stimulus indicator may include a substrate, an indicator layer having an indicator material, and a reference layer having a reference material. The reference layer and the indicator layer may be either in the same layer or in parallel layers. The indicator material and the reference material may be color-changeable in response to an environmental stimulus. The environmental stimulus may be selected from the group consisting of peak temperature, cumulative temperature, humidity, pH, radiation, ultraviolet radiation, and combinations thereof. In some embodiments, the color change of the indicator material and the reference material may be irreversible and at least one of a change in color, color density, fluorescence, or opacity. The environmental stimulus indicator may be configured to provide an indication of an environmental stimulus that is not possible if only the indicator material were color-changeable and the reference material were not color-changeable.

In some embodiments, the indication of an environmental stimulus may be an extended period of time over which the color-changing environmental stimulus indicator is able to monitor the environmental stimulus. In other embodiments, the indication of an environmental stimulus may be a shortened response period during which the color-changing environmental stimulus indicator monitors the environmental stimulus. In some embodiments, the indication of an environmental stimulus may be the combined effect of at least two environmental stimuli. The two environmental stimuli may be selected from the group consisting of temperature and radiation, temperature and pH, and temperature and humidity.

These and other features are disclosed in greater detail in the accompanying figures and the Detailed Description below.

BRIEF DESCRIPTION OF THE DRAWINGS

FIG. 7 is a table of optical density measurements measured over a period of days at 45° C.

DETAILED DESCRIPTION

Figure 1:
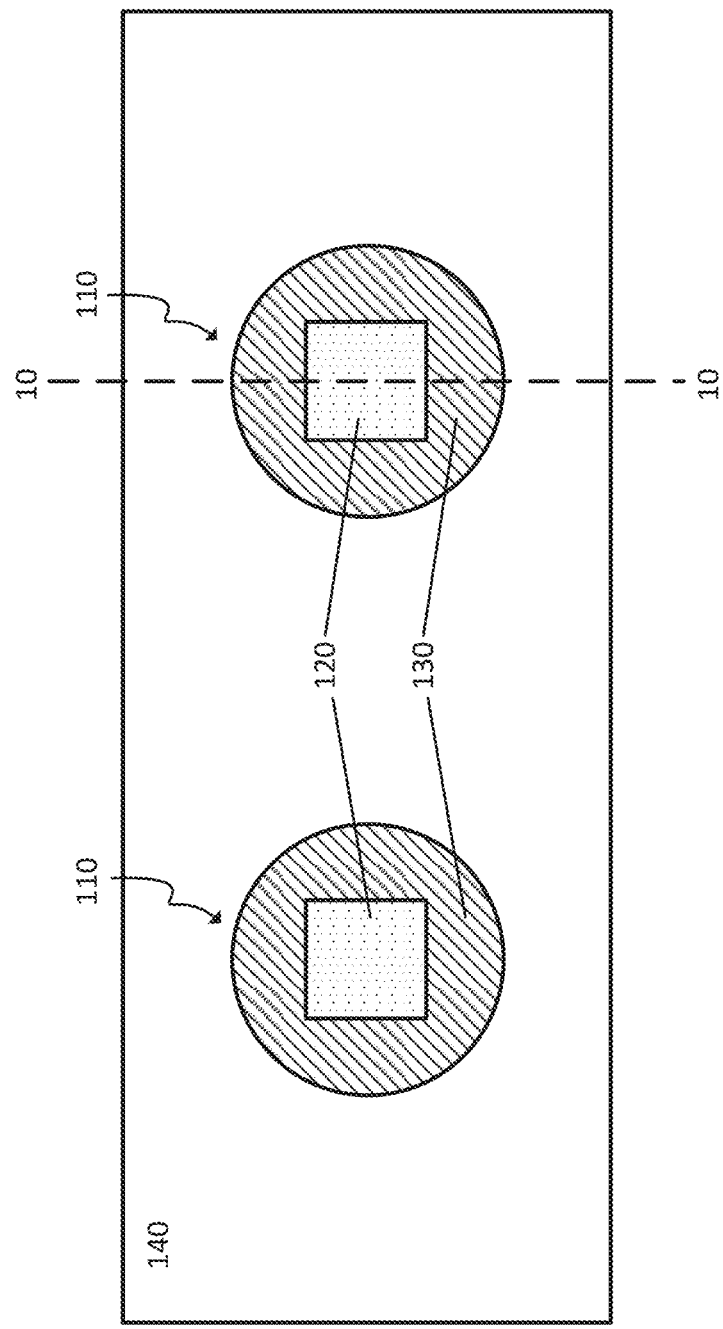
FIG. 1 is a plan view of an environmental indicator according to the present disclosure.

Described herein are new and innovative color-changing environmental stimulus indicators having a color changing reference. As discussed above, conventional environmental indicators only provide either a constant/fixed-color reference against which the active indicator is periodically compared, or a scale or legend against which the progress of the active indicator is accessed. In conventional indicator technology, indicators typically can only be adjusted to reach its end point within a specific time window, such as in 2 to 5 days, and the indicators cannot be designed to respond outside that window, such as in 1 day or 6 days. Therefore, conventional indicators may be matched to certain environmental response characteristics of a host product, but there might be other environmental response characteristics that would be difficult to be matched with conventional indicators. For example, an indicator that is made of diacetylenic monomer having an activation energy of about 26 kcal/mol and medium reactivity may be matched well with one type of vaccines, but new vaccines may be better matched if the indicator has similar reactivity with higher activation energy, about 29 kcal/mol.

Aspects of the present disclosure may address such deficiency by providing a reference that independently changes color in response to exposure to an environmental stimulus. For example, an environmental stimulus indicator may include an active indicator and a reference component, and both the active indicator and the reference component may change color in response to an environmental stimulus. The environmental stimulus may be one or more of temperature, cumulative temperature, humidity, pH, and ultraviolet radiation. In some embodiments, the active indicator and the reference component may change color in response to the same environmental stimulus. In other embodiments, the active indicator and the reference component may change color in response to a different environmental stimulus. In some embodiments, both the active indicator and the reference component may be configured to darken (or lighten), preferably at a different rate, in response to exposure to the environmental stimulus (e.g. cumulative temperature). In this case, the environmental indicator with a color changing reference may have a longer lifetime as a result of the reference becoming darker (or lighter) with time, than an environmental indicator with a constant reference. In other embodiments, the active indicator may be configured to darken (or lighten) in response to exposure to the environmental stimulus while the reference component may be configured to lighten (or darken) in response to exposure to the environmental stimulus. In this case, the environmental indicator may have a shorter lifetime as a result of the reference becoming lighter with time, than the environmental indicator with constant references, which may be a better match for a host product having a shorter lifetime. Aspects of the present disclosure may be also capable of designing an environmental indicator having a desired activation energy (e.g., 29 kcal/mol) and reactivity, for example, by combining the active indicator with a color changing reference having an activation energy (e.g., 18 kcal/mol) different from that of the active indicator (e.g., 25 kcal/mol).

In some cases, a host product to be monitored may be damaged by multiple environmental conditions. Aspects of the present disclosure may be capable of designing an environmental indicator that can monitor multiple environmental conditions, too. For example, if an environmental indicator has an active indicator configured to darken in response to exposure to one condition (e.g., temperature) and a reference component configured to lighten in response to exposure to another condition (e.g., humidity), then that indicator may reach an end point if either or both conditions occur.

Aspects of the present disclosure may be also capable of offsetting the effect of some irrelevant conditions on the active indicator. For example, a host product may not be affected by moisture but the active indicator may be moisture sensitive. Actually, some diacetylenes are slightly more reactive at low humidity. In this case, an environmental indicator may be designed to have a reference component configured to change color (e.g., darken or lighten) in response to exposure to the low humidity to offset the effect of the low humidity on the active indicator.

In some embodiments, the indicators may be employed to monitor the freshness of vaccines, drugs, fresh or processed fish, meats, and other foodstuffs as well as industrial products such as solder paste. Such indicators can also be used to monitor the maturity of products such as cheese, fruits, aged meat, wines, and the like. The indicators may provide a history of the conditions to which a host product has been exposed.

Usefully, the indicators are responsive to a wide range of ambient temperatures to which an intended host product or products, and an indicator itself, may be exposed during their monitored lives. Typically, useful indicators can respond to the cumulative time-temperature exposure which a host product experiences. To this end, the indicators can be physically associated in close proximity with the host product in a manner intended to give the indicator the same temperature exposure experience, or other condition, as the host product. In some embodiments where the indicator is mounted on the outside of a host product or product package, it may be desirably slightly conservative, responding to higher temperature events a little more quickly than the host product by virtue of its external exposure.

According to some embodiments that utilize indicator inks, the inks include indicator compositions comprising a dispersion of a particulate indicator agent in a liquid vehicle. The indicator agent can be colored or can polymerize to provide a colored appearance, or may have another visual appearance or exhibit an appearance change upon polymerization and thus resemble a pigment in having an ability to reflect light. The indicator ink can include other compounds or materials dissolved or dispersed in the liquid vehicle, as described herein, or as will otherwise be apparent, for example a reactivity-enhancing adjuvant. If desired, other useful components of the ink, or supplements or auxiliaries thereto, may be provided in other physical phases or media—for example, one or more layers—that are associated with the primary ink components in the end product.

"Ambient temperature" and "ambient thermal conditions" as used herein include a range of temperatures to which a host product may be exposed during storage and transportation, display, and other events that may occur during its useful life. Ambient temperatures may include normal and abnormal indoor room temperatures as well as outdoor temperatures in a variety of weather conditions, "Ambient temperature" can usually be understood to be the temperature or temperatures of a surrounding environment, often that of, or close to that of, the air in a room, storage chamber, vehicle, display case, warehouse or the like, as opposed to the temperature of a heat applying device such as a hot print head.

While widely distributed products may encounter either or both hot climates or cold climates, it is to be expected that indicator agents that exhibit measurable responses at room temperature will have greater responses at higher temperatures. Accordingly, to be useful for monitoring exposure of a host product to a range of ambient temperatures, room-temperature or near-room-temperature reactivity can be a desirable attribute of materials to be used as indicator agents. To this end, references herein to "ambient temperature reactivity" and equivalent phrases, are to be understood to include measurable, useful, or significant reactivity at temperatures below 50° C., for example reactivity at a temperature of 37° C. (99° F.), of 25° C. (77° F.), of 20° C. (68° F.) or at other useful temperatures.

Host products may on occasion be exposed to temperatures as high as 70° C. (158° F.), perhaps only briefly, but for most purposes thermal indicators may need to be responsive at room temperature or even lower temperatures.

It will be understood that their reactivity at lower rather than higher temperatures can be a useful selection factor in determining the value of materials as time-temperature indicator agents. Some materials having good low-temperature reactivity may be of particular use for monitoring more perishable products—for example, meats and fish—that are commonly stored at cold temperatures of, for example, about 5° C. (41° F.) and below.

The environmental indicators of the present disclosure may utilize and combine any number of indicator technologies. The present disclosure outlines a number of different technologies though a person of ordinary skill in the art would readily understand the applicability of the present principles to other indicator technologies. The technologies disclosed herein include color-changing inks—such as diacetylene monomers—etching technologies, light scattering compositions—such as meltable solids dispersed in a medium, and multi-phase compositions.

Color-Changing Inks

Indicator agents useful in the presently disclosed indicators can comprise chemically active groups or moieties that can respond, preferably irreversibly, to thermal or other ambient conditions, to provide a clearly perceptible change in appearance. Some indicator agents can be polymerizable compounds such as polyacetylenic compounds or other compounds capable of providing suitable responses. Some compounds are susceptible to adjuvant-mediated reactivity enhancement. Other chemical compounds that are substantially inactive, showing little or no response to thermal or other conditions at ambient temperatures—for example temperatures below 50° C.—but which display useful appearance-changing responses to exposure to higher temperatures when utilized with a suitable reactivity-enhancing adjuvant may also be employed to provide desired thermal response characteristics in the end product indicator.

The term "polyacetylenic" as used herein to qualify "indicator agent," "compounds," "monomers," or other materials is to be understood to reference or include acetylenic compounds having at least two conjugated acetylene groups per molecule. Examples of such polyacetylenes include diynes, triynes, tetraynes, and hexaynes.

Useful embodiments of polyacetylenic compounds include substituted diacetylenic compounds for example diacetylenes (R—C≡C—C≡C—R, where R is a substituent group). Examples of R groups include alkyl, aryl, benzoates, sulfonates, urethanes, acids, alcohols, and the like.

Polyacetylenic compounds useful for monitoring ambient conditions are sometimes described in the art, with more or less precision, as "monomers," "diacetylenic monomers," or "substituted diacetylenic monomers." All such diacetylenic materials that can provide a detectable indication of exposure to an environmental condition, optionally on a cumulative basis, are to be understood to be included by the term "diacetylenic agent" as it is used herein.

It should be noted that although the term "monomer" is sometimes used to denote active acetylenic monitor component materials intended to be employed in time-temperature indicators ("TTIs"), dimeric and polymeric component compounds derived from a similar basic structure can also be employed. The term "polyacetylenic agent" as used herein is intended to embrace various such reactive diacetylenic compounds that are capable of polymerizing in response to conditions of interest while providing a useful detectable parameter change, notably, but not exclusively, a distinct visual change. Other parameters, for example electrical parameters such as conductivity, dielectric constant, or the like might be detected, if desired, and the invention can also employ reactive acetylenic agents capable of providing such other changes in response to relevant parameter changes.

Many compounds useful as indicator agents that provide an irreversible indication of cumulative thermal exposure and which may be employed in the disclosed embodiments are disclosed in the Patel, Preziosi and other patents cited herein. The disclosures of Patel U.S. Pat. No. 3,999,946 at column 4, line 13, to column 5, line 48 and of Preziosi et al. U.S. Pat. No. 4,788,151 at column 3, line 58, to column 4, line 62, are incorporated by reference herein. In the disclosures incorporated from these documents, references to "the invention," "preferred," "preferably," and the like are to be understood to refer to the invention of the respective cited patent rather than to the embodiments disclosed herein.

Spontaneously polymerizable diacetylenic monomers useful in the presently disclosed embodiments include compounds having, or complying with, the following formula:

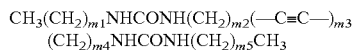

wherein m1 is 0 or is a positive integer in the range of from 1 to about 17:
   m2 is a positive integer in the range of from 1 to about 10:
   m3 is a positive integer in the range of from 2 to 4:
   m4 is a positive integer in the range of from 1 to about 10: and
   m5 is 0 or is a positive integer in the range of from 1 to about 17.

In some embodiments, m2, m3, and m4 can be the same integer, and there can be differences between m1 and m5 in the two monomers, if desired. For example, one of m1 or m5 in one of the monomers can differ from the other one of m1 or m5 in the other monomer, respectively.

In some embodiments, both of m1 and m5 in one of the monomers can differ from m1 and m5 in the other monomer. If desired, m3 can be two. In some embodiments, m1 and m5 can be 1 in the first monomer and 2 in the second monomer and m2 and m4 can both be 1.

Other useful broad definitions of the first monomer and the second monomer will be apparent to a person of ordinary skill in the art in light of this disclosure, or will become apparent in the future, as the art develops.

One group of useful polymerizable diacetylenic monomers and which may have favorable toxicology characteristics comprises substituted 2,4-hexadiyn-1,6-bis(alkylurea) compounds wherein the alkyl group is selected from the group consisting of ethyl-, propyl-, butyl-, octyl-, dodecyl-, and octyldecyl-substituted 2,4-hexadiyn-1,6-bis(alkylurea) compounds, and the foregoing compounds wherein the alkyl substituents are linear.

Some specific examples of useful compounds in this group include: 2,4-hexadiyn-1,6-bis(ethylurea) ("KE"); 2,4-hexadiyn-1,6-bis(propylurea) ("KPr"); and co-crystallized acetylenic agents, such as a 2:1 co-crystallized mixture of 2,4-hexadiyn-1,6-bis(ethylurea) and 2,4-hexadiyn-1,6-bis (propylurea) monomers ("KX monomer").

The term "diacetylenic monomer composition" is used herein to include compositions comprising two, or possibly more than two, diacetylenic monomers having distinctly different chemical structures. An example of a diacetylenic monomer composition comprises a mixture of 2,4-hexadiyn-1,6-bis(ethylurea) and 2,4-hexadiyn-1,6-bis(propylurea). The chemical structure of 2,4-hexadiyn-1,6-bis (propylurea) differs from that of 2,4-hexadiyn-1,6-bis(ethylurea) by two methylene groups (one in each substituent group of the monomer molecule).

U.S. Publication No. 2009/0131718 to Baughman et al. ("Baughman"), the disclosure of which is incorporated by reference herein, relates to crystal structures, crystallization methods, methods of characterization, uses, possible modes of polymerization and other useful information regarding certain 2,4-hexadiyn-1,6-bis(alkylurea) compounds useful as monomers in the products and methods of the present disclosure. In light of this disclosure, it will be understood by a person of ordinary skill in the art that certain insights, understanding or description regarding individual diacetylenic monomers that appears in Baughman can be applied, mutatis mutandis, to the co-crystallized diacetylenic monomers and related methods of the present disclosure.

Another class of compounds that may be employed comprises polymerizable diacetylenic compounds that provide a visual change at higher temperatures but which are thermally insensitive or inactive at or near room temperature. Some examples of such compounds include: 2,4-hexadiyn-1,6-diol bis(phenylurethane) 2,4-hexadiyn-1,6-diol bis(p-methoxybenzene sulfonate); 9-(N-carbazolyl)-5,7-nonadiyn-1-ol phenylurethane; o,o'-diacetylenyldiphenyl glutarate; 2,4-hexadiyn-1,6-diol-bis-p-toluene sulfonate; and 2,4-hexadiyn-1,6-diol-bis-(p-chlorobenzene sulfonate).

Some examples of polymerizable diacetylenic compounds with substantially no, or only low, thermal reactivity at ambient temperatures, that may be employed, with suitable adjuvants, are disclosed in Wegner et al. "Topochemical Reactions of Monomers with Conjugated Triple Bonds" 9 J. POLY. SCI.B.POLY. LETTERS 133-44 (1971) ("Wegner 1971"). Such compounds include (N,N'-diacetyl)-diam ino-diphenyldiacetylenes and di-(phenylureido)-diphenyldiacetylenes. Neither the para-diacetyl-substituted compound nor any of the ortho-, meta- or para-di-phenyl diureido compounds displays any significant reactivity at elevated temperatures such as 180° C., according to Wegner 1971.

Some further examples of polymerizable diacetylenic compounds that lack heat sensitivity at typical ambient temperatures, and which may be employed when accompanied by suitable adjuvants are described in Wegner, "Topochemical Polymerization of Monomers with Conjugated Triple Bonds" 154 DIE MAKROMOLECULARE CHEMIE 35-48 (1972) ("Wegner 1972"), for example in the results tables on pages 39 and 42.

Additional inactive diacetylenic compounds may be commercially available or can be obtained or prepared by methods known in the art. Some examples of such compounds and methods are described in Patel et al. U.S. Pat. No. 3,999,946 or 4,228,126; Ivory U.S. Pat. No. 4,298,348; and Roth U.S. Pat. No. 6,524,000.

The disclosures of Roth at column 4, line 48 to column 5, line 35 and at column 3, lines 13 to 28 are incorporated by reference herein. Inactive polymerizable diacetylenic compounds can be prepared, as described by Roth, from more active diacetylenic compounds or mixtures by melt recrystallization or solvent recrystallization with rapid cooling or by other methods.

A variety of adjuvants can be employed, alone or in combination, to enhance the reactivity of polyacetylenic indicator agents. Useful reactivity enhancements may comprise an increase in thermal reactivity or thermal responsiveness. For example, the indicator agent may polymerize faster at a given temperature. In some embodiments, a sharper end point or other useful reactivity enhancement may be obtained. For example, the response profile of the indicator agent may be modified so that polymerization occurs more rapidly near a desired end point, so as to provide a sharper end point. Sharper end points may be helpful in providing a clear indication of a particular host product condition, for example imminent loss of freshness, or of an accumulation over time of one or more ambient conditions that is often associated with the particular host product condition.

Broadly stated, useful reactivity enhancement of useful polymerizable polyacetylenic indicator compounds may comprise an increase or decrease in polymerization reaction rate, an increase or decrease in activation energy, a change in the shape of the time-temperature response curve of the indicator compound, or a combination of two or more of the foregoing parameters, for example an increase in reaction rate combined with an increase in activation energy and a response curve modification providing a sharper end point. The particular enhancement obtained in a given case will depend upon the particular combination of indicator agent and adjuvant system employed.

The diversity of response parameters that can be achieved enables a skilled person to better match an indicator composition to the environmental response characteristics of a host product.

It is generally desirable for suitable adjuvant materials to be effective at ambient temperatures and to be capable of being formulated into inks that can be applied to paper, card, plastic or other suitable substrate materials in desired patterns to provide visual indicators, including time-temperature indicators. The adjuvant or adjuvant system or compound may have good solubility in a liquid ink vehicle suitable for thermally sensitive indicator inks, for example an organic solvent.

Under conditions inducing polymerization, many diacetylenic monomer molecules become chained together to form a polydiacetylene. The reaction takes place in the solid state and is irreversible. In some cases, colorless, or nearly colorless, crystals of the diacetylenic monomer, or monomers, are transformed into intensely colored crystals of polymer in response to sufficient cumulative thermal exposure or another environmental condition. The polymerization reaction can proceed spontaneously, at rates largely determined by the ambient conditions and the characteristics of the monomer materials.

Because the polymerization reaction is irreversible, the color change resulting from polymerization is also irreversible under normal conditions. This property is useful in indicators for monitoring perishable products, such as vaccines, food, or medicines that may lose quality after excessive cumulative thermal exposure. Diacetylenic monomers can also be employed as the active agents in indicators used for monitoring the maturity of maturing products, for example wine or cheese. For these and other purposes, the diacetylenic monomer can be incorporated as the active agent in an indicator label or card, or other indicator device, to be associated with a host product to be monitored. The indicator device provides a color change signal, derived from polymerization of the diacetylenic monomer, which can be perceived by a human viewer at a convenient viewing distance, for example by a medical professional administering a vaccine or medicament, or a shopper selecting a food product from a refrigerated display in a supermarket. A reversible indicator may not be useful for such purposes.

Etching Technologies

According to some embodiments of an environmental indicator, a chemical reaction such as etching may be used. An example of an etching process whose progression is affected by environmental conditions is the etching of metal layers, such as aluminum, copper, or zinc. Some embodiments of a cumulative exposure indicator where the substrate comprises or includes a thin metal layer (e.g., aluminum, copper, or zinc layer), an etchant may be included that is configured to etch away the metal layer over time with exposure to heat so as to reveal the underlying substrate. The cumulative exposure indicator may include a barrier coating configured to initially separate the etchant from the metal layer and to control the rate at which the etchant reacts with the metal layer. The etchant may be contained within a pressure-sensitive laminating adhesive layer.

Meltable Solids

Another example embodiment of the invention is a heat indicator for monitoring ambient heat exposure traversing a threshold temperature that employs a coalescable particulate colored material that has a small particle size and is initially light-colored due to light scattering, and which darkens in response to an ambient heat exposure event traversing the threshold temperature. The threshold temperature may be a peak temperature, a freezing temperature or another suitable temperature.

In some embodiments, the meltable particulate colored material has an average particle size imbuing the meltable particulate colored material with a light color, the light color being attributable to scattering of visible light by the meltable colored material particles, wherein melting of the meltable particulate colored material causes the peak exposure indicator to change its visual appearance, the change in appearance being induced by an ambient heat exposure peak reaching a temperature exceeding the melting point of the meltable particulate colored material. Light scattering may be caused or influenced by, in some embodiments, air gaps between the meltable particulate material that is suspended in a binder material.

Multi-Phase Compositions

Breakdown of a three-phase dispersion can be used as an operating principle for a temperature condition indicator. Generally, the indicator can comprise an indicator dispersion which contains two miscible phases which are separated by a barrier phase. Thus, an indicator dispersion can comprise a base phase; a barrier phase dispersed in the base phase; and an active phase dispersed in the barrier phase. Typically, the active phase is miscible with the base phase, the barrier phase is not completely soluble in, or is substantially insoluble in, the base phase, and the active phase is not completely soluble in, or is substantially insoluble in, the barrier phase. Thus, the barrier phase effectively separates the active phase from the base phase so that base phase does not substantially mix with the active phase as long as the dispersion is intact. Other configurations of indicator dispersion may be used that operate on the same principle. For example, the relative amounts, relative particle sizes, number of particles, and/or other parameters may be varied while utilizing the same basic principle.

The dispersion can remain intact until a temperature condition is met. If the temperature condition is met, the dispersion can break down, or some other change can occur, so that a significant amount of mixing will occur between the active phase and the base phase to form a combined phase. If the combined phase is formed, a detectable and irreversible change in an apparent color of the indicator dispersion will occur. Thus, this detectable and irreversible change in apparent color allows a potential user to discern if a temperature condition has occurred that could cause a product to be spoiled.

In some embodiments, the barrier phase may have a solubility in the base phase that is less than about 1%, less than about 0.01%, less than about 0.001%, or less than about 0.0001%.

In some embodiments, the active phase may have a solubility in the barrier phase that is less than about 1%, less than about 0.01%, less than about 0.001%, or less than about 0.0001%.

For example, an o/w/o emulsion or a w/o/w emulsion could be used. For an o/w/o emulsion, the oil phase dispersed in the water phase is the active phase, the water phase is the barrier phase, and the oil phase in which the water phase is dispersed is the base phase. For a w/o/w emulsion, the water phase dispersed in the oil phase is the active phase, the oil phase is the barrier phase, and the water phase in which the oil phase is dispersed is the base phase. Similar assignments can be made to other three-phase emulsions containing other types of phases that are not oil or water. A three-phase dispersion could also include a solid phase instead of being an emulsion. For example, such a dispersion could have a liquid oil base phase, an aqueous barrier phase, and a hydrophobic solid active phase. Alternatively, an indicator dispersion could have an aqueous base phase, a hydrophobic solid barrier phase, and an aqueous active phase.

This type of three-phase dispersion can be used to detect many types of temperature condition, such as a threshold temperature (a high temperature and/or a low-temperature threshold), a phase transition (such as freezing or melting), or a thermal history, such as an elevated temperature for a particular period of time or a depressed temperature for a particular period of time. Thus, a three-phase dispersion can be used for any kind of temperature condition indicator, such as a threshold temperature, including a high temperature threshold indicator or a low-temperature threshold indicator, a thermal history indicator, a freeze indicator, a melt indicator, or a combination thereof.

There are two basic factors that can affect how an indicator dispersion operates. First, the cause or mechanism of mixing of the active and base phases can determine, or can be used to select, what type of temperature condition the indicator dispersion is used to detect. Second, the manner in which mixing between the active phase and the base phase affects color can determine, or can be used to select, the nature of the apparent color change.

For some indicator dispersions, mixing between the active phase and the base phase can be a result of freezing. For example, when the water in an o/w/o emulsion freezes, the active oil phase and the base oil phase can coalesce and mix. Similarly, if water in a w/o/w emulsion freezes, the base phase may freeze first because the likelihood of nucleation decreases as volume decreases. As the base phase freezes, water forms ice crystals that grow, forcing the oil droplets closer, which may result in partial or complete coalescence of the oil phase. The coalesced oil phase may rise to the top of the frozen base phase. Since water expands upon freezing, the base phase can compress the oil phase, which can cause the w/o emulsion of the barrier and aqueous phase to break so that, upon thawing, the active phase and the base phase can mix.

For some indicator dispersions, mixing between the active phase and the base phase can be a result of melting. For example, if a dispersion has a solid wax barrier phase, melting of the wax can cause the aqueous active phase to coalesce into the aqueous base phase.

For some indicator dispersions, mixing between the active phase and the base phase can be a result of phase inversion between the active phase and the barrier phase or inversion between the barrier phase and the base phase. For example, some surfactants, such as non-ionic surfactants, have a hydrophilic-lipophilic balance (HLB) that varies with temperature. The HLB value is a measure of the relative hydrophilicity or lipophilicity of a surfactant. A surfactant that is more soluble in water than in oil will have an HLB value greater than 10, and a surfactant that is less soluble in water than in oil will have an HLB value of less than 10.

In an emulsion, the continuous phase tends to be the phase in which the surfactant is more soluble. Thus, surfactants with a low HLB value tend to form water-in-oil (w/o) emulsions. Surfactants with a high HLB value tend to form oil-in-water (o/w) emulsions. Thus, if the HLB value of the surfactant is dependent upon temperature, an emulsion can invert as a result of a significant temperature change. For example, some surfactants, such as some non-ionic surfactants, can have a low HLB value (e.g., less than about 6) at higher temperatures, which can produce a w/o emulsion at higher temperatures. The same surfactant can have a high HLB value (e.g., greater than about 10) at lower temperatures. This can cause a w/o emulsion formed at a higher temperature to invert to an o/w at a significantly lower temperature as the HLB value increases. Thus, if a w/o/w emulsion comprising such a surfactant experiences a temperature drop to a threshold temperature, the oil barrier phase and the aqueous active phase can invert so that the aqueous base phase and the aqueous active phase are combined. Alternatively, if a w/o/w emulsion comprising such a surfactant experiences a temperature increase to a threshold temperature, the aqueous base phase and the oil barrier phase can invert so that the aqueous active phase and the aqueous base phase are combined. Similar inversions can occur with o/w/o emulsions. Solid emulsion stabilizers, such as Pickering emulsifiers, may also have emulsion inversion properties.

One method or mechanism for causing a detectable and irreversible change in apparent color of the indicator dispersion by mixing the active phase and the base phase is light scattering. For example, the active phase and/or the barrier phase may have a particle size in a range that results in a significant amount of light scattering, which may change, reduce, or even substantially eliminate the appearance of the natural color of a colorant in the active phase.

For example, light scattering can mask a color, such as a dark color, so light scattering causes a colorant to appear lighter than it would normally appear. When a colored material, such as a colorant, is present in the active phase that is dispersed as small particles within the barrier phase, some light may be scattered so that it has less contact with the colored compound or material. Thus, the color can appear different, for example, less intense than the natural color of the colorant. Scattering may also affect the apparent color or hue of a colorant in a dispersion, for example making a dispersion appear more red (e.g. making an orange appear more red, or a yellow appear orange) or blue (e.g. making a yellow appear greenish or a green appear blue) than the natural color of the colorant. Scattering may also affect the apparent color or hue of a background viewed through a dispersion. Thus, the apparent color may be substantially lighter or otherwise different due to light scattering, while the natural color itself does not change.

Color includes achromatic visual appearances, for example, black, gray, and white, and chromatic visual appearances, including primary color hues, secondary color hues and/or other color hues, for example, without limitation, red, yellow, green, blue, purple, orange, brown, etc. The natural color of the colorant refers to the appearance of the colorant, including, intensity, shade, tint, hue, etc., in the same medium and at the same concentration or amount without any scattering effect. The term "color change" and its grammatical variants are used to refer to changes in hue, intensity or lightness (or darkness) or other changes in visual appearance.

For some indicator dispersions, the active phase or the barrier phase can have a droplet size such that, before the temperature condition is met, light scattering affects the apparent color of the indicator dispersion. The active phase can have a colorant that is not present in the base phase before the two phases mix. Thus, when the temperature condition is met, mixing of the active phase and the base phase can cause the colorant to be introduced into the base phase and color the newly formed combined phase. The colorant that is in the combined phase should not be affected by light scattering in the same way that the colorant in the active phase was before the temperature condition was met. As a result, the color of the combined phase, or the color of the indicator dispersion in general, appears different. Thus, a temperature condition may be detected by a color change with respect to the apparent color of the indicator dispersion or the combined phase. In some embodiments, the color of the combined phase, or the color of the indicator dispersion in general, appears darker.

Mixing of the active phase and the base phase or breakdown of the dispersion can have an effect on apparent color that goes beyond transfer of a colorant from one phase to another. Mixing of the active phase and the base phase can also affect the light scattering properties of the dispersion. For example, the size of the particles of the active phase and/or the barrier phase could become larger, which could change the light scattering properties of the dispersion. Additionally, although for convenience we refer to the system as the indicator dispersion after mixing of the active phase and the base phase, the dispersion may no longer exist at this point, which could significantly reduce the scattering effect or eliminate it altogether. Thus, mixing the active phase and the base phase can cause a change in light scattering that can contribute to the detectable and irreversible change in the apparent color of the indicator dispersion.

Upon mixing of the active and the base phase, a substantial amount of, or substantially all of, the active phase of the indicator dispersion may no longer be dispersed in the barrier phase. Similarly, upon mixing of the active and the base phase, a substantial amount of, or substantially all of the barrier phase may no longer be dispersed in the base phase. Thus, the indicator dispersion can be broken to form a two phase system comprising the barrier phase and a combined phase formed from the active phase and the base phase, wherein the two phases are substantially not dispersed in one another. After the temperature condition is met, when the emulsion is broken, the indicator can appear blotchy rather than uniform.

For an indicator dispersion having a color change affected by light scattering, an active phase may have any droplet size that results in light scattering by the active phase and/or the barrier phase so that light scattering at least partially masks or alters the color of the colorant. Scattering may increase as the size of dispersed particles decreases. For example, it can be helpful if the aqueous active phase has an average droplet size near the wavelength range of visible light, such as about 10 nm to about 2000 nm, about 100 nm to about 1200 nm, about 350 nm to about 900 nm, or about 390 nm to about 700 nm.

It is helpful if a colorant in an active phase is dispersible or soluble in the medium of the active phase and the base phase to the extent that the natural color of the colorant may be observed as a result of mixing between the active phase and the base phase.

An opacifying agent may be used to effect a change in apparent color upon mixing of the base phase and the active phase. For example, a colorant could be present in the active phase but not the base phase. An opacifying agent could be present in the barrier phase, which can cause the dispersion to be opaque so that the inherent color of the colorant is at least partially masked by the opacity of the indicator dispersion. Mixing of the active phase and the base phase can transfer the colorant to the base phase, so that at least a portion of the colorant is less obscured by the opacifying agent because the clarity of the base phase is less obscured by the barrier phase than is the active phase and/or because the dispersion is broken.

An opacifying agent could be any pigment or dye that is dispersible or soluble in the barrier phase. Examples of useful opacifying agents include oxides, sulfides, carbonates and the like of titanium, cerium, zirconium, magnesium, iron, manganese, calcium, cadmium, tin, barium and the like. In some embodiments, the opacifying agent is titanium oxide.

A change in apparent color may also be due to a chemical reaction which occurs if the active phase mixes with the base phase. This may be because the active phase contains an agent which is reactive with some component present in the base phase. Alternatively, the active phase could comprise a first active sub-phase comprising a first chemically active agent and a second active sub-phase comprising a second chemically active agent. Each particle of the active phase would contain only the first chemically active agent or the second chemically active agent. Thus, the barrier phase would separate the first active sub-phase from the second active sub-phase. If mixing between the active phase and the base phase occurred, particles from both the first active sub-phase and the second active sub-phase would mix with the base phase. Therefore, the first chemically active agent and the second chemically active agent can be present together in the combined phase so that the chemical reaction occurs in the combined phase.

Any type of two (or more) component chemical reaction can be used, provided that the reaction results in the color change. For example, some color-changing chemical reaction, such as acid-base reactions, are affected by pH. Some color-changing chemical reactions are oxidation-reduction reactions.

A useful class of oil soluble compounds showing intense color change on reaction is leuco dyes. These include compounds whose molecules can acquire two forms, one of which is colorless, or light colored, and the other of which is colored, sometimes strongly colored. The colorless form of a leuco dye can include substantially colorless compounds having a skeletal lactone, lactam, sulfone, spiropyran, ester or amido structure, including triarylmethane compounds, bisphenylmethane compounds, xanthene compounds, thiazine compounds, spiropyran compounds, and the like.

Examples of leuco dyes include, but are not limited to, crystal violet lactone. On development with a suitable leuco dye developer, examples of which are described elsewhere herein, crystal violet lactone forms a deep blue or violet color.

Some further examples of useful leuco dyes include products described as specialty magenta 20, ODB-1 and ODB-2 which are available from Emerald Hilton Davis, Cincinnati, Ohio and PERGASCRIPT® Red 16B available from BASF, Charlotte, N.C. Specialty magenta 20 and PERGASCRIPT® Red 16B produce an intense magenta color. Color precursors ODB-1 and ODB-2, upon development, become black.

Combinations of two or more mutually compatible leuco dyes can be employed. Combinations of crystal violet lactone and specialty magenta 20 can produce colors that can range from magenta to deep purple.

In addition to being detectable by observation by a person, the effect of light scattering, opacifying, or any other color changing effect on a natural color can be detected by an optical instrument. An optical instrument includes any device that can detect a change in apparent color of an indicator dispersion. Some optical instruments may detect the effect of light scattering on a natural color by detecting a change in the spectrum of visible light absorbed by, emitted by, or reflected from, an indicator dispersion.

A change in apparent color can be associated with, or related to, a change in a visible light spectrum of an indicator dispersion. For some indicators, a person observing the indicator dispersion will see a color that results from light that passes into or through the indicator dispersion, and is reflected back to the observer. Light scattering can cause a significant amount of light to be reflected back without being absorbed by the colorant in the indicator dispersion. This can cause the dispersion to appear lighter, white, translucent, or milky. It can also affect the visible light absorption spectrum of the indicator dispersion.

A visible light absorption spectrum of a sample can be taken by obtaining a spectrum of incident light that is reflected from or through a sample. If no scattering occurs, the absorption spectrum will be a plot of the amount of light absorbed that would otherwise be reflected back by or through the sample at the various wavelengths in the visible range. If scattering occurs, light that would otherwise be absorbed can be scattered back to the detector of the spectrometer instead of being absorbed, which can result in a lower absorbance in the absorption spectrum for wavelengths of light that are scattered, as compared to a sample where scattering does not occur. Thus, light scattering can be detected by comparison of a visible light absorption spectrum of the colorant in a single phase medium to a visible light absorption spectrum of the colorant in a light scattering emulsion, where the amount of the colorant, in mass per unit volume, is the same for the two samples.

Normally, an indicator dispersion will have the same amount of colorant, in mass per unit volume, before and after mixing of the active phase and the base phase. Thus, for some indicators, if an indicator dispersion meets a temperature condition, it can be detected by a change in the absorption spectrum caused by opacification, a color change of a component in the indicator dispersion, a loss of light scattering, or other change in light scattering, associated with the mixing of the active phase and the base phase. Although the effect of scattering on the spectrum of an indicator dispersion that emits light can be different than absorbance, scattering can also affect the emission spectrum of an emissive indicator emulsion. Thus, a change in a visible spectrum of an indicator emulsion can be a basis for detecting a temperature condition using an optical instrument, such as visible light absorption spectrometer, or a visible light fluorescent or phosphorescent spectrometer.

In addition to instruments such as spectrometers, changes in the apparent color or the spectrum of an indicator dispersion caused by meeting a temperature condition can often be detected by instruments that are not spectrometers, such as scanners, bar code readers, smart phones, etc.

Optical density can be expressed by the formula $$OD_\lambda = \log_{10}(I_0/I)$$

where I is the intensity of light at a specified wavelength A that is reflected by a sample and $I_0$ is the intensity of the light before it enters the sample In some embodiments, a 1 mm path of the indicator dispersion is at least about 0.05, at least about 0.1, at least about 0.2, at least about 0.4, at least about 1, or at least about 2 optical density units darker after a temperature condition is met, wherein the optical density is darker at a wavelength in the range of about 380 nm to about 700 nm, about 380 nm to about 450 nm, about 450 nm to about 550 nm, about 550 nm to about 570 nm, about 570 nm to about 580 nm, about 590 nm to about 700 nm, about 380 nm to about 400 nm, about 400 nm to about 420 nm, about 420 nm to about 440 nm, about 440 nm to about 460 nm, about 460 nm to about 480 nm, about 480 nm to about 500 nm, about 500 nm to about 520 nm, about 520 nm to about 540 nm, about 540 nm to about 560 nm, about 560 nm to about 580 nm, about 580 nm to about 600 nm, about 600 nm to about 620 nm, about 620 nm to about 640 nm, about 640 nm to about 660 nm, about 660 nm to about 680 nm, or about 680 nm to about 700 nm.

A change in apparent color can be quantified by a change in one or more of three tristimulus values X, Y, and Z, as measured with a tristimulus colorimeter, such as one made by Hunter Labs. A measured difference in tristiumulus values may refer to the dispersion before a temperature condition is met as compared to the combined phase after a temperature condition is met, the emulsion before a temperature condition is met as compared to the barrier phase after a temperature condition is met, or the emulsion before a temperature condition is met as compared to some combination of the barrier phase, the combined phase, the active phase, and the base phase after a temperature condition is met. In some embodiments, the value of X changes after a temperature condition is met. In some embodiments, the value of Y changes after a temperature condition is met. In some embodiments, the value of Z changes after a temperature condition is met. In other embodiments some or all of the tristimulus values change in concert with each other.

A change in apparent color can also be quantified by a change in hiding power as measured with a Pfynd Cryptometer. In some embodiments, the hiding power may change after a temperature condition is met. In some embodiments the wet hiding power may change by several mil (several thousands of an inch); for example an emulsion might have wet hiding power value of 6 mil prior to a temperature condition is met, i.e. a wet film 6 mil in thickness obscures the difference between black and white backgrounds, while the same emulsion after a temperature condition is met might have a wet hiding power value of 15 mil or more.

DISCUSSION OF THE FIGURES

FIG. 1 depicts example environmental indicators according to the present disclosure. Multiple environmental indicators 110 may be embodied as labels and may be supported on a liner 140 for production in quantity. Various other configurations of environmental indicator 110 are possible. FIG. 1 shows a section of liner 140 on which a number of environmental indicators 110 may be arranged in series, for mass production of the environmental indicators, using print industry technology, or packaging industry technology, or the like. Such label example embodiments may be produced at low cost in self-adhesive configurations and may be suitable for attachment to the outer surface of a mass-produced host product, or to packaging or a container for the host product. The environmental indicator 110 may include an active indicator 120 and a reference component 130. The structure of the environmental indicator is described in greater detail below and as shown in FIG. 2.

Figure 2:
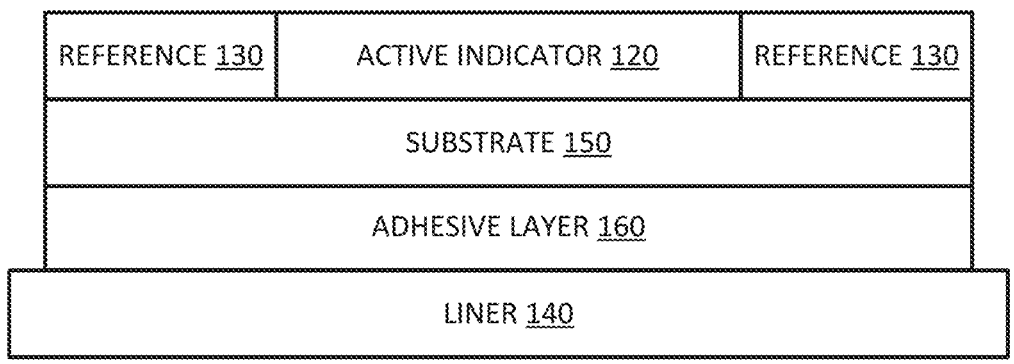
FIG. 2 is a cross-sectional view of an environmental indicator according to the present disclosure.

FIG. 2 is a cross-sectional view taken along imaginary line 10-10 in FIG. 1 which demonstrates that environmental indicator 110 may comprise a substrate 150, bearing an adhesive layer 160, which may be pressure sensitive, and which removably adheres substrate 150 to liner 140, so that environmental indicator 110 may be applied to a host product or a package or carton. For this purpose, liner 140 may be a release liner that is coated with a suitable low surface energy material to facilitate removal of adhesive-coated substrate 150. In some embodiments, the active indicator 120 and the reference component 130 may be placed on the substrate 150. In some embodiments, the reference component 130 may be configured in a ring extending around the active indicator 120, or in another suitable configuration (not shown) alongside or near the active indicator 120. In some embodiments, the reference component 130 may be a color changing material placed on top of a constant-color material (not-shown). In other embodiments, the reference component 130 may be a single color changing material. In other embodiments, the reference component 130 may be a combination of color-changing and non-color changing materials. The appearances of the active indicator 120 and the reference component 130 may be optically read by a human viewer or by a suitable image processing device, for example, a camera.

In some embodiments, a transparent film (not shown) may overlie the active indicator 120 and the reference component 130 to provide protection from physical abrasion or abuse. Transparent film may be secured to the active indicator 120 and the reference component 130 by a layer of adhesive (not shown), or in another suitable manner. Transparent film may bear printed indicia providing identifying or instructional, or other information regarding the environmental indicator and/or an associated host product. Transparent film may be sufficiently transparent that the active indicator 120 and the reference component 130 may be viewed and that the colors and changes in the color or optical density at the active indicator 120 and the reference component 130, may be viewed and/or optically read.

The environmental indicator 110, active indicator 120, and/or reference component 130 may have any desired shape. The shapes, considered independently, may be circular, square, rectangular, triangular, hexagonal, polygonal, elongated, circular, oval, elliptical, strip-like, another regular shape, an irregular shape, a shape representing a recognizable image such as a check mark, or another suitable shape. As shown in FIG. 1, by way of example, the reference component 130 may be circular and the active indicator 120 may be configured as a square within the circle of reference component 130.

As shown in FIG. 2, the environmental indicator 110 may have a layered structure. The shapes and relative dimensions of the various layers may be varied significantly. One example embodiment of the environmental indicator 110 has thin, laminar layers to provide a low-profile device that may have a compact configuration and may be applied to small host products such as vaccine vials and the like.

The size of the environmental indicator 110 may vary according to the intended application, or for other purposes. Some example embodiments of such a environmental indicator may have a largest transverse dimension in the range of from about 5 mm to about 30 mm, for example, from about 10 mm to about 15 mm.

In some embodiments, the active indicator 120 and the reference component 130 may be color changeable in response to an environmental stimulus. The environmental stimulus may be one or more of temperature, cumulative temperature, humidity, pH, and ultraviolet radiation. In some embodiments, the active indicator 120 and the reference component 130 may change color in response to the same environmental stimulus. In other embodiments, the active indicator 120 and the reference component 130 may change color in response to different environmental stimuli. In some embodiments, the active indicator 120 or the reference component 130 may be a time-temperature indicator, a temperature threshold indicator, a cumulative indicator, a heat indicator, a freeze indicator, a melt indicator, a pH indicator, a UV indicator, or a combination of two or more of the foregoing indicators.

In some embodiments, the active indicator 120 may be configured to darken in response to exposure to the environmental stimulus while the reference component 130 may be configured to lighten in response to exposure to the environmental stimulus. For example, the active indicator 120 may be configured to darken in response to exposure to cumulative temperature, while the reference component 130 may be configured to lighten in response to exposure to the cumulative temperature. In this case, the environmental indicator may have a shorter lifetime as a result of the reference becoming lighter with time, than the environmental indicator with constant references, which may be a better match for a host product having a shorter lifetime. In other embodiments, both the active indicator 120 and the reference component 130 may be configured to darken or lighten in response to exposure to the environmental stimulus. In some embodiments, the active indicator 120 and the reference component 130 may change color in response to exposure to the environmental stimulus at a different rate. In other embodiments, the active indicator 120 and the reference component 130 may change color in response to exposure to the environmental stimulus at the same or similar rate.

In some embodiments, the active indicator 120 and/or the reference component 130 may be a color changing ink, such as a diacetylene. In other embodiments, the active indicator 120 and the reference component 130 may change color by using one or more techniques including metal etching, dye diffusion, and acid/base reactions. In some embodiments, the reference component 130 may help a viewer or viewing device judge the state of the active indicator 120 by having an appearance similar to the appearance of the active indicator 120 at an end point. The end point appearance may be an appearance that indicates a probable condition of an associated host product, for example, that the host product has lost efficacy or quality and should not be used.

In some embodiments, the color change may be a change in color, color density, fluorescence, and/or opacity. In some embodiments, the color change of the active indicator 120 and/or the reference component 130 may be irreversible. The color change of the active indicator 120 and/or the reference component 130 may occur after a predetermined cumulative exposure to the environmental stimulus. In some embodiments, the reference component 130 may change color (e.g., darken or lighten) with time.

In some embodiments, the environmental indicator 110 may include an ultraviolet radiation filter configured to protect the active indicator 120 and/or the reference component 130 from exposure to ultraviolet radiation. For example, the transparent film discussed above may include an ultraviolet filter material to filter, or block incident ultraviolet radiation.

In some embodiments, the active indicator 120 may be configured to change color in response to exposure to cumulative temperature (e.g., time-temperature indicator) and the reference component 130 may be configured to change color in response to exposure to a temperature near or below a predetermined temperature (e.g., freezing temperature). In other embodiments, the active indicator 120 may be configured to change color in response to exposure to cumulative temperature and the reference component 130 may be configured to change color in response to exposure to humidity.

In some embodiments, the color changing environmental indicator may exhibit an optical density difference of 0.4 OD between the before-activation and the after-activation appearances of the active indicator and the reference component, providing a distinct color change and good contrast. Higher optical differences, for example, 0.5 OD or 0.6 OD, or higher, may also be exhibited. In some embodiments, the environmental indicator may exhibit an optical density difference of 0.2 OD or 0.3 OD between the before-activation and the after-activation appearances of the active indicator and the reference component, also providing a distinct color change.

Figure 3:
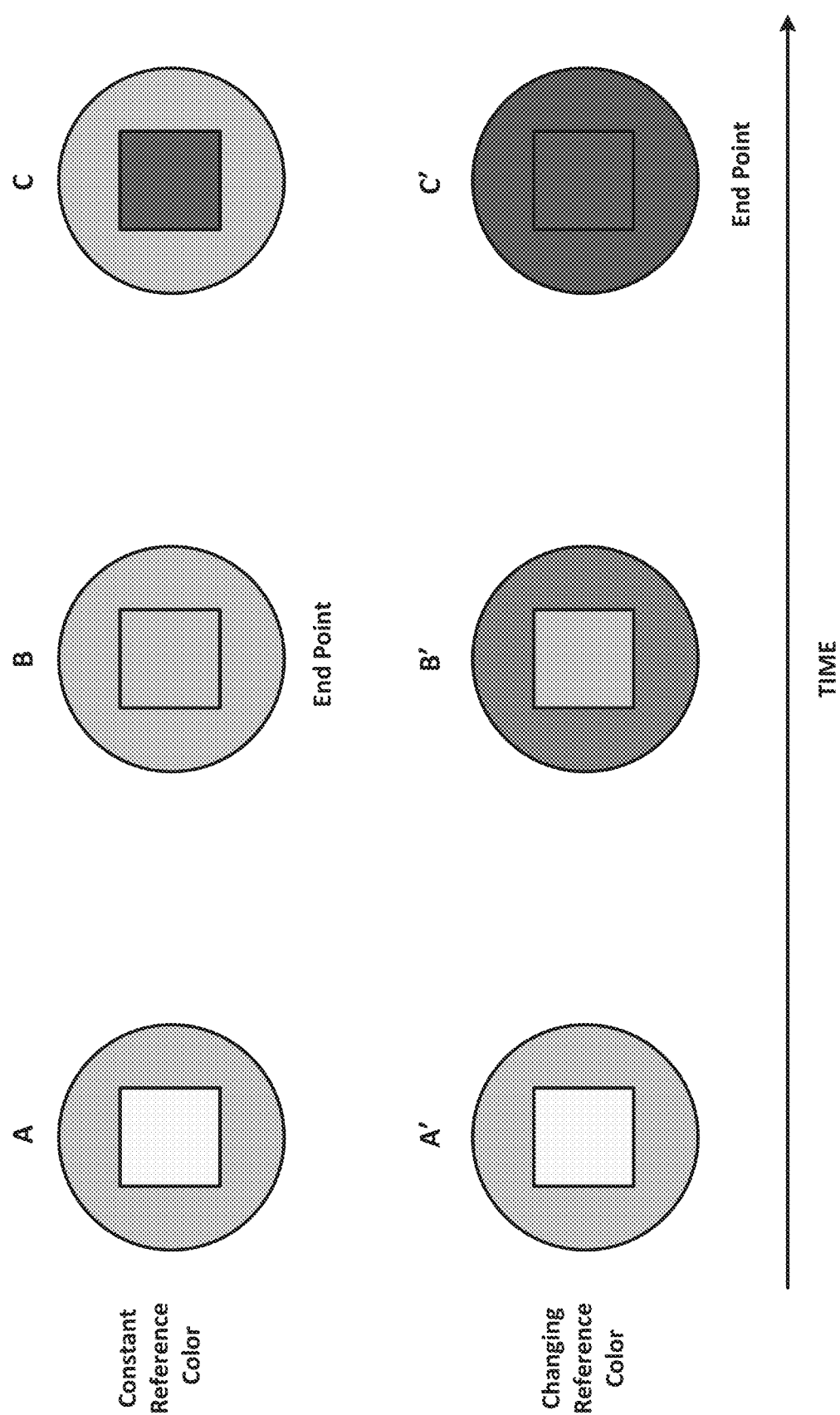
FIG. 3 is an illustration of the visual change over time of an environmental indicator with a changing reference compared against an environmental indicator with a constant reference.

FIG. 3 illustrates the visual change over time of an environmental indicator with a changing reference compared against an environmental indicator with a constant reference. Assuming that both environmental indicators have active indicators with the same active rate of color change with time (inner square becoming darker), the environmental indicator with a changing reference color may have a longer lifetime as a result of the reference becoming darker with time, than the environmental indicator with a constant reference. For example, in case of the environmental indicator with a constant reference, the end point may occur at B (or B') while the environmental indicator with a changing reference may have an end point at C (or C') which is later than B (or B'). If the active indicator technology can only be adjusted to reach its end point within a specific time window such as in 2 to 5 days, then the indicator itself cannot be designed to respond outside that window, such as in 1 day or 6 days. Simply making the constant reference darker may shift the time window from 2-5 days to, for example, 7-10 days, but it would not extend the time window itself (e.g., 2-8 days). Aspects of the present disclosure may address such deficiency by providing a reference that independently changes color in response to exposure to an environmental stimulus. Therefore, aspects of the present disclosure may be capable of extending the limits (e.g., time window) more than they would be extended for just the active indicator and enable an environmental indicator to have a longer lifetime than an indicator with a constant reference.

Figure 4A:
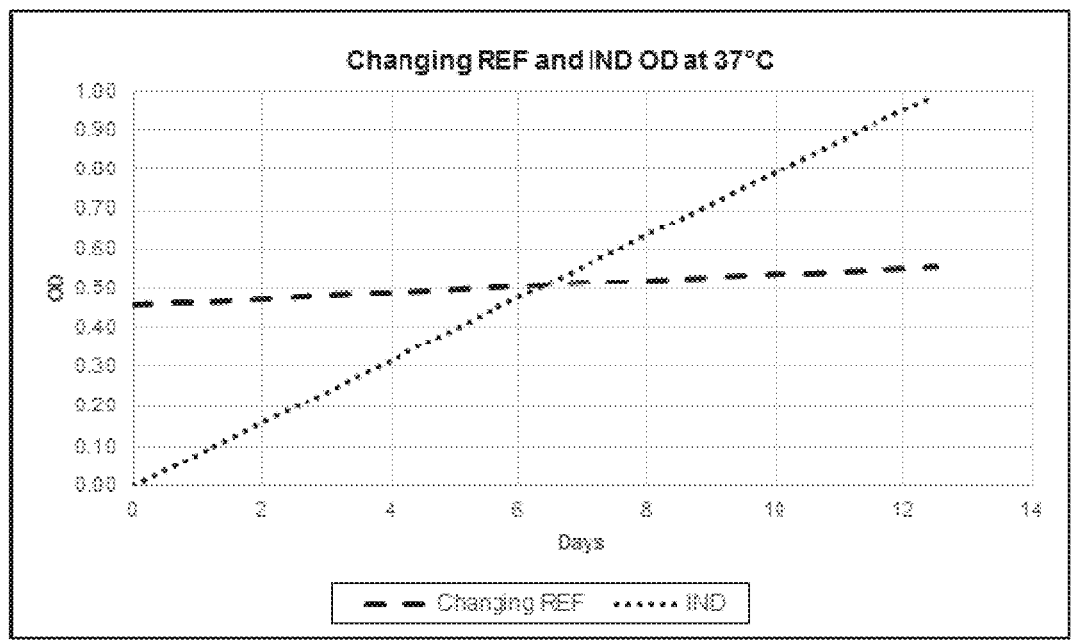
FIGS. 4A-4B are simulated graphs illustrating the change in optical density of environmental indicators with changing references.
Figure 4B:
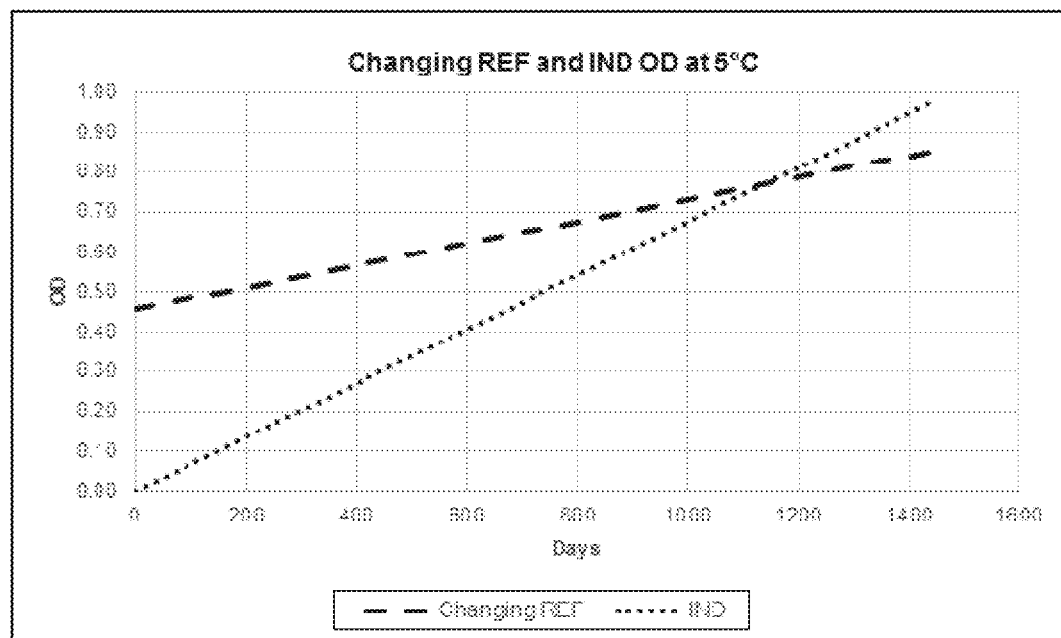

FIGS. 4A and 4B show simulated graphs illustrating the change in optical density of environmental indicators with changing references at 37° C. and 5° C. In this simulation, it is assumed that both the active indicator and the reference component are time-temperature indicators and become darker in response to exposure to time-temperature. It is also assumed that the active indicator has an activation energy of ~26 Kcal/mol and the reference component has an activation energy of ~18 Kcal/mol. As shown in FIGS. 4A and 4B, the environmental indicator needs approximately 7 days at 37° C. or approximately 1100 days at 5° C. to reach the end point.

Figure 5A:
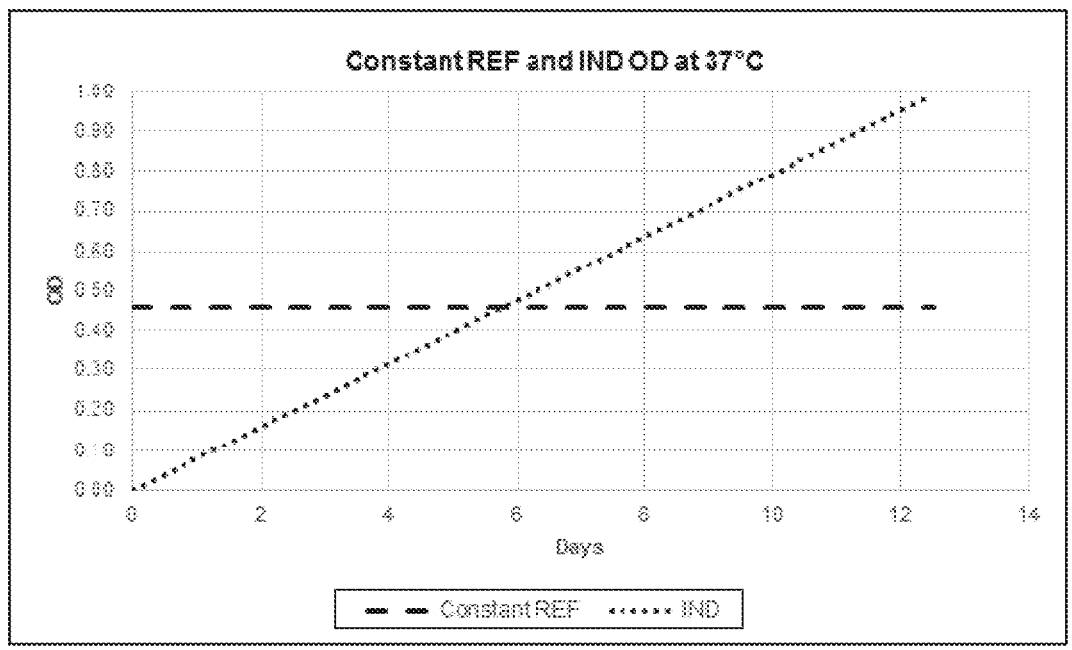
FIGS. 5A-5B are simulated graphs illustrating the change in optical density of environmental indicators with constant references.
Figure 5B:
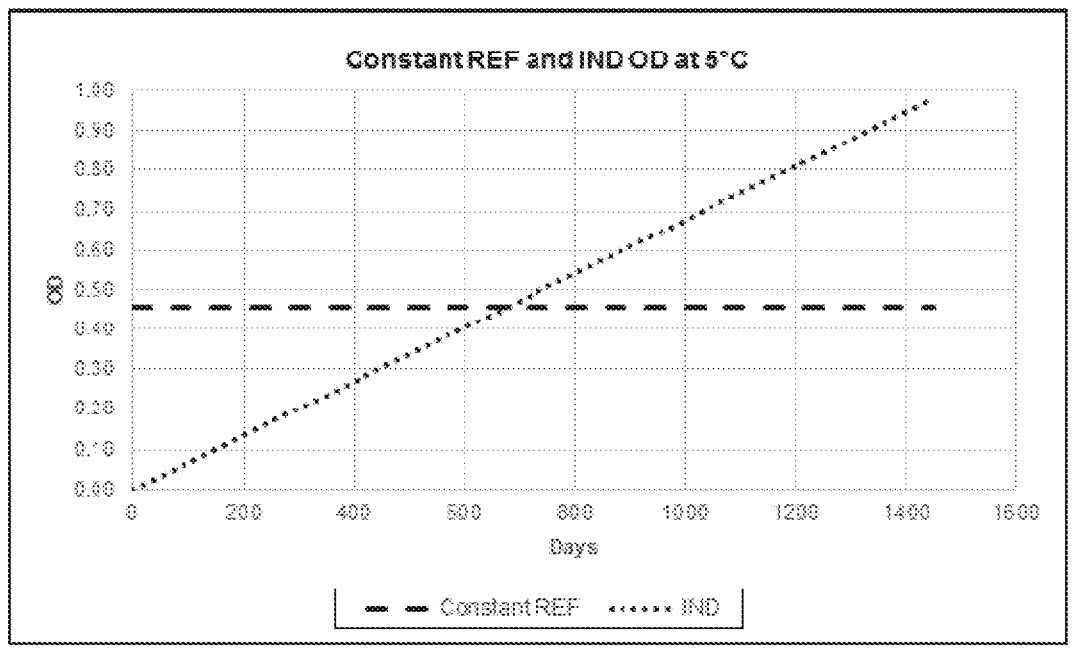

FIGS. 5A-5B are simulated graphs illustrating the change in optical density of environmental indicators with constant references. The simulated graphs show that, in case of a similar environmental indicator with the same active region (~26 Kcal/mol) but with a non-changing reference, the end point would reach approximately at 6 days at 37° C. or approximately 700 days at 5° C.

Figures 6A, 6B:
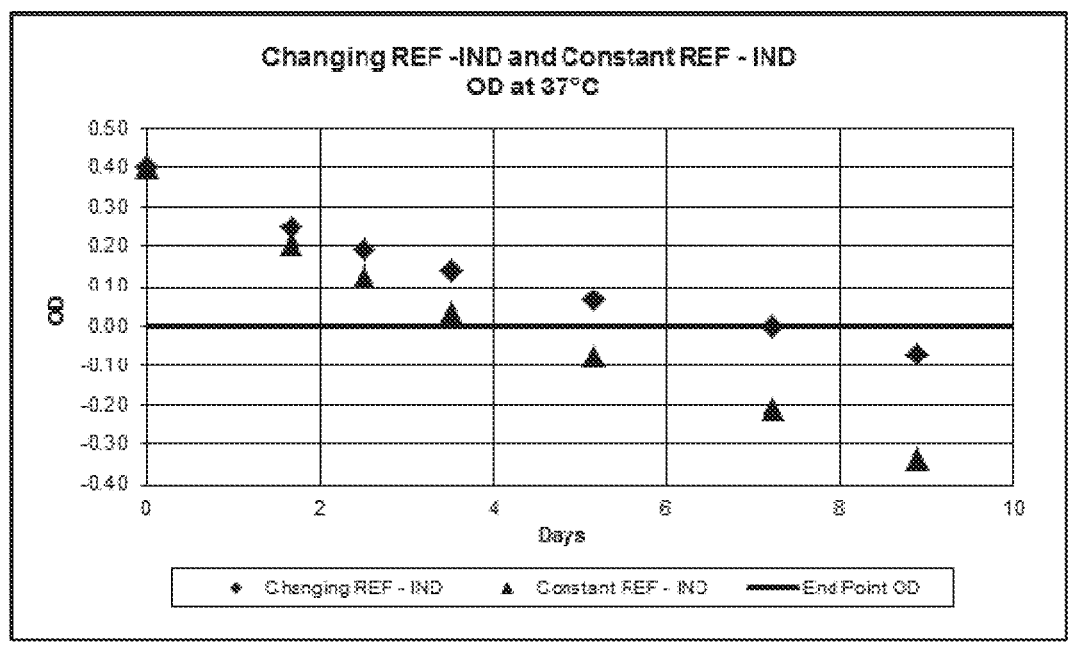
FIG. 6A is a table of optical density measurements measured over a period of days at 37° C.
FIG. 6B is an empirical graph illustrating the change in optical density of an environmental indicator with a changing reference compared to the change in optical density of an indicator with a constant reference.

FIG. 6A is a table of optical density measurements measured over a period of days at 37° C. FIG. 6B is an empirical graph illustrating the change in optical density of an environmental indicator with a changing reference compared to the change in optical density of an indicator with a constant reference. The tabulated data in FIG. 6A was used to construct the graph in FIG. 6B. KE active monomer was used for both the active indicator and the reference component. As shown in FIGS. 6A and 6B, the end point of the environmental indicator with a changing reference reached approximately at 7 days at 37° C. However, the end point of the environmental indicator with a constant reference reached approximately at 4 days at 37° C. This result shows that the indicator lifetime was extended by approximately three days as a result of introducing the changing reference.

As shown in FIG. 7, which is a table of optical density measurements measured over a period of days at 45° C., similar conclusions could be obtained from measurements taken at 45° C. At 45° C., the end point of the environmental indicator with a changing reference reached approximately at 2.5 days, while the end point of the environmental indicator with a constant reference reached approximately at 1.5 days.

Figure 8:
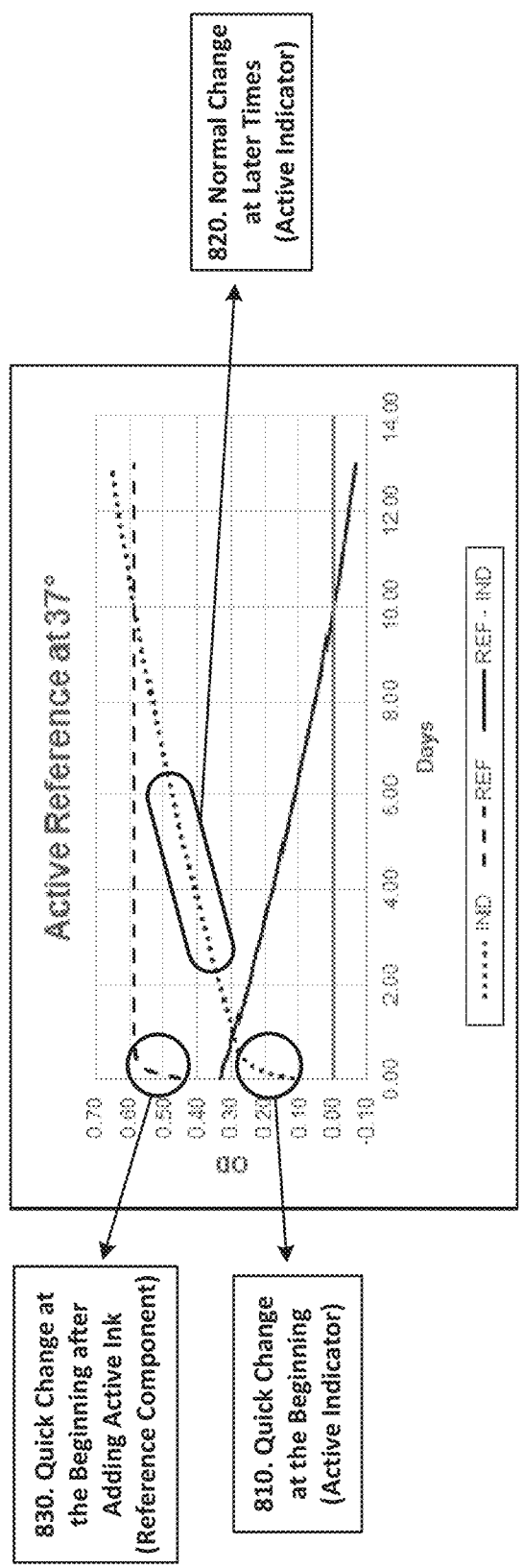
FIG. 8 is a simulated graph illustrating the change in optical density of an indicator material and a reference material.

FIG. 8 is a simulated graph illustrating the change in optical density of an indicator material and a reference material. In some cases, the active region of an environmental indicator darkens much more quickly at the beginning (810) than at later times (820), so the OD of the reference minus the active indicator (REF−IND) changes faster than desired at the beginning. As shown in FIG. 8, adding an active ink, which changes color quickly at the beginning and then stabilizes at later times in response to exposure to an environmental stimulus, such as time-temperature, to the reference component (see 830) may offset the quick change of the active indicator at the beginning.

EXAMPLES

The following examples are specifically contemplated by the author(s) of the present disclosure:

Example 1

Active indicators typically have a specific activation energy that cannot be adjusted (as is the case for many chemical families). Due to this limitation, this indicator technology was typically only used to monitor host products that matched its activation energy in the past. For example, a certain diacetylenic monomer (or diacetylenic ink) used for an active indicator has an activation energy of about 26 kcal/mol and medium reactivity which is ideal for most traditional vaccines. However new vaccines would be better matched if the environmental indicator has similar reactivity with higher activation energy, about 29 kcal/mol.

In this example, by introducing a reference that darkens over time with a lower activation energy (e.g. 18 kcal/mol) than that of the diacetylene monomer described above, (e.g. 26 kcal/mol), the environmental indicator had an effective activation energy higher than 26 kcal/mol (e.g. 29 kcal/mol). For example, when both the active indicator and the reference component are configured to darken in response to exposure to cumulative temperature at a different rate (e.g., the active indicator and the reference component have different activation energies: e.g., active indicator—26 kcal/mol; reference—18 kcal/mol), then the environmental indicator had a higher effective activation energy (e.g. 29 kcal/mol) than the active indicator. In some embodiments, the active indicator is configured to darken in response to exposure to cumulative temperature and the reference component is configured to lighten in response to exposure to the cumulative temperature such that the color-changing environmental stimulus indicator may have a lower effective activation energy than the active indicator alone. Therefore, aspects of the present disclosure may enable an environmental indicator to have an activation energy that conventional active indicator materials could not have, by combining the active indicator with a color changing reference having an activation energy different from that of the active indicator.

In the simulated graphs in FIGS. 4A, 4B, 5A, and 5B, discussed above, the active indicator has an activation energy of ~26 Kcal/mol and the reference component has an activation energy of ~18 Kcal/mol. As shown in the figures, the environmental indicator with a color changing reference needs approximately 7 days at 37° C. and approximately 1100 days at 5° C. to reach the end point, while the environmental indicator with a constant reference needs approximately 6 days at 37° C. and approximately 700 days at 5° C. This result shows that the indicator lifetime was extended by approximately 1 day at 37° C. and 400 days at 5° C. as a result of introducing the changing reference and, thus, this environmental indicator having a higher effective activation energy (e.g. 29 kcal/mol) may have a longer lifetime.

Example 2

In some embodiments, the material used for the active indicator and the reference component may be sensitive to ultraviolet radiation as well as temperature. That is, the active indicator and the reference component may become dark in response to exposure to ultraviolet radiation and temperature. For example, some diacetylenes may darken rapidly when exposed to ultraviolet radiation. If the host product is affected by temperature, but not by ultraviolet radiation, this may create a problem. For example, the active indicator may reach an end point well before the host product loses its freshness, and thus, fail to provide a correct indication of the host product condition. In this example, a temperature-insensitive monomer may be coated over the reference component to match the darkening of the active indicator in the presence of ultraviolet light. Then, both the active indicator and the reference component may darken in the presence of light (e.g., UV light), while only the active indicator may change color as a result of temperature or heat exposure. Therefore, the present example is capable of offsetting the effect of ultraviolet radiation to the active indicator when the material used for the active indicator is sensitive to ultraviolet radiation.

Example 3

In some cases, a host product to be monitored may be damaged not only by temperature, but also by humidity, pH, and/or ultraviolet radiation. In this example, an environmental indicator may have an active indicator configured to darken in response to exposure to one condition (e.g., temperature) and a reference component configured to lighten in response to exposure to another condition (e.g., humidity). Then, this environmental indicator may be able to reach an end point if either or both conditions occur. There can be various designs for an environmental indicator with changing references, which is sensitive to two environmental conditions (one condition for active indicator and another condition for reference component) as shown in Table 1 below:

TABLE 1

| | Sensitive Conditions | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| IND | tmp | tmp | tmp | hum | hum | hum | pH | pH | pH | UV | UV | UV |
| REF | hum | pH | UV | tmp | pH | UV | tmp | hum | UV | tmp | hum | pH |

(IND = Active Indicator; REF = Reference Component; tmp = temperature; hum = humidity)

It is also possible that the active indicator and/or the reference component are sensitive to more than one condition (e.g., active indicator—temperature and humidity; reference component—pH and UV). Then, there can be various designs for an environmental indicator that is sensitive to more than three environmental conditions (e.g., temperature, humidity, pH, and UV) as shown in Table 2 below:

TABLE 2

| | Indicator A | Indicator B |
|---|---|---|
| 1 | temperature | humidity, pH, UV |
| 2 | humidity | temperature, pH, UV |
| 3 | pH | temperature, humidity, UV |
| 4 | UV | temperature, humidity, pH |
| 5 | temperature, humidity | pH, UV |
| 6 | temperature, pH | humidity, UV |
| 7 | temperature, UV | humidity, pH |
| 8 | temperature, humidity | pH |
| 9 | temperature, humidity | UV |
| 10 | temperature, pH | Humidity |
| 11 | temperature, pH | UV |
| 12 | temperature, UV | Humidity |
| 13 | temperature, UV | pH |
| 14 | humidity, pH | temperature |
| 15 | humidity, pH | UV |
| 16 | humidity, UV | temperature |
| 17 | humidity, UV | pH |
| 18 | pH, UV | temperature |
| 19 | pH, UV | humidity |

In some embodiments, indicator A is the active indicator and indicator B is the reference component. In other embodiments, indicator A is the reference component and indicator B is the active indicator.

Example 4

In some cases, a host product is not affected by moisture but the active indicator technology is itself moisture sensitive. For example, some diacetylenes are slightly more reactive at low humidity. Then, a color changing reference component can be used to offset the effect of moisture on the active indicator. For example, an environmental indicator may be designed to have an active indicator configured to change color (e.g., darken or lighten) in response to exposure to temperature and low humidity and a reference component configured to change color (e.g., darken or lighten) in response to exposure to the low humidity. Then, the reference component would offset the effect of the low humidity to the active indicator. In some embodiments, an environmental indicator may be designed to offset the effect of other conditions, such as pH, high humidity, and UV. For example, an environmental indicator may be designed to have an active indicator configured to change color (e.g., darken or lighten) in response to exposure to temperature and one or more other conditions (e.g., pH, high humidity, and UV) and a reference component configured to change color (e.g., darken or lighten) in response to exposure to the one or more other conditions (pH, high humidity, and UV) to offset the effect of the one or more other conditions on the active indicator.

In some embodiments, the environmental indicator may be used for a host product (not shown) and/or a container containing the host product. The environmental indicator may be attachable to the container. Examples of host products include vaccines, drugs, medication, pharmaceuticals, cosmeceuticals, nutricosmetics, nutritional supplements, biological materials for industrial or therapeutic uses, food stuffs, medical devices, prophylactics, cosmetics, beauty aids, and perishable munitions and ordnance.

EMBODIMENTS

The authors of the present disclosure contemplate a number of diverse embodiments including at least the following:

Embodiment 1

A color-changing environmental stimulus indicator comprising:
a substrate;
an active indicator placed above the substrate; and
a reference component;
wherein the active indicator and the reference component are color changeable in response to an environmental stimulus;
wherein the color change of the active indicator and the reference component occurs after a predetermined cumulative exposure to the environmental stimulus.

Embodiment 2

The color-changing environmental stimulus indicator of embodiment 1, wherein the reference component includes an active ink configured to change color quickly at the beginning of the exposure and stabilize at later times.

Embodiment 3

The color-changing environmental stimulus indicator of embodiment 1 or 2,
wherein the active indicator and the reference component change color in response to the same environmental stimulus; or
wherein the active indicator and the reference component change color in response to different environmental stimuli; or
wherein the active indicator is configured to darken in response to exposure to the environmental stimulus and the reference component is configured to lighten in response to exposure to the environmental stimulus; or
wherein the active indicator is configured to lighten in response to exposure to the environmental stimulus and the reference component is configured to darken in response to exposure to the environmental stimulus; or
wherein both the active indicator and the reference component are configured to darken or lighten in response to exposure to the environmental stimulus; or
wherein the reference component is configured to change color with time.

Embodiment 4

The color-changing environmental stimulus indicator of embodiment 1, 2 or 3, wherein at least one of the active indicator and the reference component change color by using a technique selected from the group consisting of a color changing ink, metal etching, dye diffusion, acid/base reactions, and combinations thereof.

Embodiment 5

The color-changing environmental stimulus indicator of embodiment 1, 2, 3, or 4, further comprising an ultraviolet radiation filter configured to protect at least one of the active indicator and the reference component from exposure to ultraviolet radiation.

Embodiment 6

The color-changing environmental stimulus indicator of embodiment 1, 2, 3, 4, or 5,
wherein the reference component is a color changing material placed on top of a constant-color material; or
wherein the reference component is a single color changing material; or
wherein the reference component is a combination of color-changing and non-color changing materials.

Embodiment 7

A color-changing environmental stimulus indicator comprising:
a substrate;
an active indicator placed above the substrate; and
a reference component,
wherein the active indicator and the reference component are configured to indicate an exposure to an environmental stimulus by changing color.

Embodiment 8

The color-changing environmental stimulus indicator of embodiment 7,
wherein both the active indicator and the reference component are configured to darken in response to exposure to cumulative temperature at different rates such that the color-changing environmental stimulus indicator has a higher effective activation energy than the active indicator; or wherein the active indicator is configured to darken in response to exposure to cumulative temperature and the reference component is configured to lighten in response to exposure to the cumulative temperature such that the color-changing environmental stimulus indicator has a lower effective activation energy than the active indicator; or wherein the active indicator is configured to lighten in response to exposure to cumulative temperature and the reference component is configured to darken in response to exposure to the cumulative temperature such that the color-changing environmental stimulus indicator has a lower effective activation energy than the active indicator; or wherein the active indicator and the reference component are configured to change color in response to exposure to ultraviolet radiation and temperature, wherein a temperature-insensitive compound is coated within or over the reference component adjust or offset the relative impact of ultraviolet light on the active indicator with respect to that of the reference component; or wherein the active indicator is configured to change color in response to exposure to temperature and humidity, and the reference component is configured to change color in response to exposure to humidity to adjust or offset the relative impact of humidity on the active indicator with respect to that of the reference component; or wherein the active indicator is configured to change color in response to exposure to cumulative temperature and the reference component is configured to change color in response to exposure to a temperature near or below a predetermined temperature.

Embodiment 9

The color-changing environmental stimulus indicator of embodiment 7 or 8, wherein the active indicator is configured to change color in response to exposure to temperature, and the reference component is configured to change color in response to exposure to at least one of humidity, pH, and ultraviolet radiation.

Embodiment 10

The color-changing environmental stimulus indicator of embodiment 9, wherein the active indicator is configured to darken in response to exposure to the temperature and the reference component is configured to lighten in response to exposure to the at least one of humidity, pH, and ultraviolet radiation.

Embodiment 11

A color-changing environmental stimulus indicator comprising:
a substrate;
an indicator layer comprising an indicator material;
a reference layer comprising a reference material;
wherein the reference layer and the indicator layer are either in the same layer or in parallel layers;
wherein the indicator material and the reference material are color-changeable in response to an environmental stimulus;
wherein the color change of the indicator material and the reference material; and
wherein the environmental stimulus indicator is configured to provide an indication of an environmental stimulus that is not possible if only the indicator material were color-changeable and the reference material were not color-changeable.

Embodiment 12

The color-changing environmental stimulus indicator of embodiment 11, wherein the indication of an environmental stimulus is an extended period of time over which the color-changing environmental stimulus indicator is able to monitor the environmental stimulus.

Embodiment 13

The color-changing environmental stimulus indicator of embodiment 11, wherein the indication of an environmental stimulus is a shortened response period during which the color-changing environmental stimulus indicator monitors the environmental stimulus.

Embodiment 14

The color-changing environmental stimulus indicator of embodiment 11, 12, or 13, wherein the indication of an environmental stimulus is the combined effect of at least two environmental stimuli.

Embodiment 15

The color-changing environmental stimulus indicator of embodiment 14, wherein the two environmental stimuli are selected from the group consisting of temperature and radiation, temperature and pH, and temperature and humidity.

Embodiment 16

The color-changing environmental stimulus indicator of embodiment 1, 2, 3, 4, 5, 6, 7, 8, 9, 10, 11, 12, 13, 14, or 15, wherein the environmental stimulus is selected from the group consisting of temperature, cumulative temperature, humidity, pH, ultraviolet radiation, and combinations thereof.

Embodiment 17

The color-changing environmental stimulus indicator of embodiment 1, 2, 3, 4, 5, 6, 11, 12, 13, 14, 15, or 16, wherein the reference component has a similar appearance to the active indicator at an end point.

Embodiment 18

The color-changing environmental stimulus indicator of embodiment 7, 8, 9, or 10, wherein the reference component is configured to have a similar appearance to the active indicator at an end point.

Embodiment 19

The color-changing environmental stimulus indicator of embodiment 1, 2, 3, 4, 5, 6, 11, 12, 13, 14, 15, or 16, wherein the color change of the active indicator and the reference component is irreversible.

Embodiment 20

The color-changing environmental stimulus indicator of embodiment 1, 2, 3, 4, 5, 6, 11, 12, 13, 14, 15, 16, or 19, wherein the color change of the active indicator and the reference component is at least one of a change in color, a change in color density, a change in fluorescence, or a change in opacity.

Embodiment 21

A stimulus-sensitive product, comprising:
a host product;
a container containing the host product; and
the color-changing environmental stimulus indicator of embodiment 1, 2, 3, 4, 5, 6, 7, 8, 9, 10, 11, 12, 13, 14, 15, 16, 17, 18, 19, or 20,
wherein the color-changing environmental stimulus indicator is attachable to the container.

Embodiment 22

The stimulus-sensitive product of embodiment 21, wherein the host product is selected from the group consisting of a vaccine, a drug, a medication, a pharmaceutical, a cosmeceutical, a nutricosmetic, a nutritional supplement, a biological material, a food stuff, a medical device, and a diagnostic device.

Embodiment 23

The stimulus-sensitive product of embodiment 21, wherein the host product is a vaccine and the container is a vaccine vial.

Embodiment 24

The stimulus-sensitive product of embodiment 21, 22, or 23,
wherein the active indicator and the reference component change color in response to the same environmental stimulus; or
wherein the active indicator and the reference component change color in response to different environmental stimuli; or
wherein the active indicator is configured to darken in response to exposure to the environmental stimulus and the reference component is configured to lighten in response to exposure to the environmental stimulus; or
wherein both the active indicator and the reference component are configured to darken or lighten in response to exposure to the environmental stimulus; or
wherein the reference component is configured to change color with time.

Embodiment 25

The stimulus-sensitive product of embodiment 21, 22, 23, or 24, wherein at least one of the active indicator and the reference component change color by using a technique selected from the group consisting of a color changing ink, metal etching, dye diffusion, acid/base reactions, and combinations thereof.

Embodiment 26

The stimulus-sensitive product of embodiment 21, 22, 23, 24, or 25, further comprising an ultraviolet radiation filter configured to protect the active indicator or the reference component from exposure to ultraviolet radiation.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. In one embodiment, the terms "about" and "approximately" refer to numerical parameters within 10% of the indicated range.

The terms "a," "an," "the," and similar referents used in the context of describing the embodiments of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the embodiments of the present disclosure and does not pose a limitation on the scope of the present disclosure. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventor(s) for carrying out the embodiments of the present disclosure. Of course, variations on these described embodiments will become apparent to those of ordinary skill in the art upon reading the foregoing description. The inventor(s) expects skilled artisans to employ such variations as appropriate, and the inventor(s) intends for the embodiments of the present disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of this disclosure so claimed are inherently or expressly described and enabled herein.

Furthermore, if any references have been made to patents and printed publications throughout this disclosure, each of these references and printed publications are individually incorporated herein by reference in their entirety.

In closing, it is to be understood that the embodiments disclosed herein are illustrative of the principles of the present disclosure. Other modifications that may be employed are within the scope of this disclosure. Thus, by way of example, but not of limitation, alternative configurations of the embodiments of the present disclosure may be utilized in accordance with the teachings herein. Accordingly, the present disclosure is not limited to that precisely as shown and described.

The invention claimed is:

1. A color-changing environmental stimulus indicator comprising:
    a substrate;
    an active indicator overlaying the substrate; and
    a reference component overlaying the substrate,
    wherein the active indicator and the reference component are configured to both be exposed to the same environmental stimulus conditions over time and are both color changeable in response to cumulative exposure over time to the environmental stimulus;
    wherein the color change of the active indicator and the reference component is irreversible and is at least one selected from the group consisting of a change in hue, a change in darkness, a change in color density, a change in fluorescence, and a change in opacity;
    wherein an end point of the environmental stimulus indicator occurs after a predetermined cumulative exposure over time to the environmental stimulus and is detectable by comparison of the active indicator to the reference component; and
    wherein the reference component is a combination of a color-changing material overlaying a non-color changing material that is visible through the color changing material in at least some color states of the color-changing material.

2. The color-changing environmental stimulus indicator of claim 1, wherein both the active indicator and the reference component are configured to darken in response to cumulative exposure over time to the environmental stimulus.

3. The color-changing environmental stimulus indicator of claim 1, wherein at least one of the active indicator and the reference component change color by using a technique selected from the group consisting of a color changing ink, metal etching, dye diffusion, acid/base reactions, and combinations thereof.

4. The color-changing environmental stimulus indicator of claim 1, further comprising an ultraviolet radiation filter configured to protect at least one of the active indicator and the reference component from exposure to ultraviolet radiation.

5. A temperature-sensitive product, comprising:
    a temperature perishable host product;
    a container containing the host product; and
    the color-changing environmental stimulus indicator of claim 1,
    wherein the color-changing environmental stimulus indicator is attached to the container.

6. The temperature-sensitive product of claim 5, wherein the host product is selected from the group consisting of a vaccine, a drug, a medication, a pharmaceutical, a cosmeceutical, a nutricosmetic, a nutritional supplement, a biological material, and a food stuff.

7. The temperature-sensitive product of claim 5, wherein the host product is a vaccine and the container is a vaccine vial.

8. The temperature-sensitive product of claim 5,
    wherein the active indicator and the reference component change color in response to the same environmental stimulus; or
    wherein the active indicator and the reference component change color in response to different environmental stimuli; or
    wherein the active indicator is configured to darken in response to exposure to the environmental stimulus and the reference component is configured to lighten in response to exposure to the environmental stimulus; or
    wherein both the active indicator and the reference component are configured to darken or lighten in response to exposure to the environmental stimulus preferably at different rates; or
    wherein the reference component is configured to change color with time.

9. The temperature-sensitive product of claim 5, wherein at least one of the active indicator and the reference component change color by using a technique selected from the group consisting of a color changing ink, metal etching, dye diffusion, acid/base reactions, and combinations thereof.

10. The temperature-sensitive product of claim 5, further comprising an ultraviolet radiation filter configured to protect the active indicator or the reference component from exposure to ultraviolet radiation.

11. The color-changing environmental stimulus indicator of claim 1, wherein both the active indicator and the reference component are configured to lighten in response to cumulative exposure over time to the environmental stimulus.

12. The color-changing environmental stimulus indicator of claim 1, wherein the reference component color changing material is placed over the reference component constant-color material, so that, when the reference component color changing material is in an initial state, the reference component constant-color material is visible through the reference component color changing material.

13. The color-changing environmental stimulus indicator of claim 1, wherein the reference component consists essentially of a single color changing material.

14. A color-changing environmental stimulus indicator comprising:
a substrate;
an active indicator placed overlaying the substrate and configured to change color in response to cumulative temperature exposure over time; and
a reference component overlaying the substrate and configured to change color in response to an environmental stimulus,
the environmental stimulus indicator having an end state determinable by comparison of the color of the reference component and the color of the active indicator,
wherein the active indicator and the reference component are together configured to indicate in the end state that cumulative temperature exposure over time has exceeded a predetermined threshold; and
wherein both the active indicator and the reference component are configured to darken in response to cumulative temperature exposure over time at different rates, the reference component having an initial color state, wherein the color-changing environmental stimulus indicator has a higher effective activation energy than a second environmental stimulus indicator with the an identical active indicator and a fixed color state reference component having a color that is the same as the initial state of the reference component.

15. The color-changing environmental stimulus indicator of claim 14, wherein the reference component is configured to change color in response to exposure to at least one of humidity, pH, and ultraviolet radiation.

16. The color-changing environmental stimulus indicator of claim 15, wherein the reference component is configured to lighten in response to exposure to the at least one of humidity, pH, and ultraviolet radiation.

17. The color-changing environmental stimulus indicator of claim 14, wherein
the active indicator is configured to darken in response to a cumulative exposure to temperature over time and the reference component is configured to lighten in response to the cumulative exposure to temperature over time such that the color-changing environmental stimulus indicator has a lower effective activation energy than the active indicator.

18. A temperature-sensitive product, comprising:
a temperature perishable host product;
a container containing the host product; and
the color-changing environmental stimulus indicator of claim 14,
wherein the color-changing environmental stimulus indicator is attached to the container.

19. A color-changing environmental stimulus indicator comprising: a substrate;
an indicator component comprising an indicator material which is color-changeable in response to cumulative temperature exposure over time;
a reference component comprising a reference material;
wherein the reference material is color-changeable in response to an environmental stimulus other than temperature;
wherein the indicator component and the reference component are configured to have the same cumulative temperature exposure over time and the same exposure to the environmental stimulus other than temperature over time;
wherein the color change of the indicator material and the reference material is irreversible and is at least one of a change in color, a change in color density, a change in fluorescence, or a change in opacity;
the environmental stimulus indicator having an end state determinable by comparison of the reference component and the indicator component; and
wherein the indicator component and the reference component are together configured to indicate in the end state that cumulative temperature exposure over time has exceed a predetermined threshold.

20. The color-changing environmental stimulus indicator of claim 19, wherein the reference component is configured to extend the period of time over which the environmental stimulus indicator is able to monitor cumulative temperature exposure compared to a second environmental stimulus indicator having an identical indicator component and a reference component that is not color changeable.

21. The color-changing environmental stimulus indicator of claim 19, wherein the reference component is configured to reduce the response time of the environmental stimulus indicator component in comparison to a second environmental indicator using an identical indicator component with a reference component that is not color changeable.

22. The color-changing environmental stimulus indicator of claim 19, wherein the reference component is color changeable responsive to temperature.

23. The color-changing environmental stimulus indicator of claim 19, wherein the reference component is color changeable responsive to an environmental stimulus selected from the group consisting of radiation, pH, and humidity.

24. A color-changing environmental stimulus indicator comprising:
a substrate;
an active indicator placed overlaying the substrate and configured to change color in response to cumulative temperature exposure over time; and
a reference component overlaying the substrate and configured to change color in response to an environmental stimulus,
the environmental stimulus indicator having an end state determinable by comparison of the color of the reference component and the color of the active indicator,
wherein the active indicator and the reference component are together configured to indicate in the end state that cumulative temperature exposure over time has exceeded a predetermined threshold; and
wherein the active indicator and the reference component are configured to darken in response to exposure to ultraviolet radiation and cumulative exposure to temperature over time, wherein a temperature-insensitive monomer is coated over the reference component to match the darkening of the active indicator in the presence of ultraviolet light.

25. A color-changing environmental stimulus indicator comprising:
a substrate;
an active indicator placed overlaying the substrate and configured to change color in response to cumulative temperature exposure over time; and
a reference component overlaying the substrate and configured to change color in response to an environmental stimulus,
the environmental stimulus indicator having an end state determinable by comparison of the color of the reference component and the color of the active indicator, wherein the active indicator and the reference component are together configured to indicate in the end state that cumulative temperature exposure over time has exceeded a predetermined threshold; and wherein the active indicator is configured to change color in response to exposure to cumulative exposure to temperature over time and low humidity, and the reference component is configured to change color in response to exposure to the low humidity and configured to offset the effect of the low humidity to the active indicator.

26. A color-changing environmental stimulus indicator comprising:

a substrate;

an active indicator placed overlaying the substrate and configured to change color in response to cumulative temperature exposure over time; and a reference component overlaying the substrate and configured to change color in response to an environmental stimulus, the environmental stimulus indicator having an end state determinable by comparison of the color of the reference component and the color of the active indicator, wherein the active indicator and the reference component are together configured to indicate in the end state that cumulative temperature exposure over time has exceeded a predetermined threshold; and wherein the active indicator is configured to change color in response to cumulative exposure to temperature over time and the reference component is configured to change color in response to exposure to a temperature near or below a predetermined temperature.

* * * * *